United States Patent
Farah et al.

(10) Patent No.: US 7,917,231 B2
(45) Date of Patent: Mar. 29, 2011

(54) DIRECTIONAL STIMULATION OF NEURAL TISSUE

(75) Inventors: Maroun Farah, Nazareth (IL); Imad Younis, Nazareth Ilit (IL)

(73) Assignee: Alpha Omega Neuro Technologies Ltd., Nazareth Ilit (IL)

(*) Notice: Subject to any disclaimer, the term of this patent is extended or adjusted under 35 U.S.C. 154(b) by 376 days.

(21) Appl. No.: 12/071,876

(22) Filed: Feb. 27, 2008

(65) Prior Publication Data

US 2008/0215125 A1  Sep. 4, 2008

Related U.S. Application Data

(63) Continuation-in-part of application No. PCT/IL2007/000983, filed on Aug. 7, 2007.

(60) Provisional application No. 60/903,533, filed on Feb. 27, 2007, provisional application No. 60/903,537, filed on Feb. 27, 2007, provisional application No. 60/849,468, filed on Oct. 5, 2006, provisional application No. 60/835,881, filed on Aug. 7, 2006, provisional application No. 60/835,890, filed on Aug. 7, 2006, provisional application No. 60/835,891, filed on Aug. 7, 2006, provisional application No. 60/835,902, filed on Aug. 7, 2006.

(51) Int. Cl.
*A61N 1/05* (2006.01)
(52) U.S. Cl. ...................................... 607/116
(58) Field of Classification Search ............ 607/115–119
See application file for complete search history.

(56) References Cited

U.S. PATENT DOCUMENTS

| 4,408,604 | A  | * | 10/1983 | Hirshorn et al. | 607/121 |
| 4,969,468 | A  | * | 11/1990 | Byers et al. | 600/373 |
| 5,649,970 | A  |   | 7/1997  | Loeb et al. |  |
| 6,052,608 | A  | * | 4/2000  | Young et al. | 600/378 |
| 6,505,078 | B1 |   | 1/2003  | King et al. |  |
| 6,609,032 | B1 |   | 8/2003  | Woods et al. |  |
| 7,047,084 | B2 | * | 5/2006  | Erickson et al. | 607/116 |
| 2003/0236557 | A1 |   | 12/2003 | Whitehurst et al. |  |
| 2004/0098074 | A1 |   | 5/2004  | Erickson et al. |  |
| 2004/0186528 | A1 | * | 9/2004  | Ries et al. | 607/36 |
| 2006/0036296 | A1 | * | 2/2006  | Greenberg et al. | 607/54 |
| 2006/0129205 | A1 |   | 6/2006  | Boveja et al. |  |

FOREIGN PATENT DOCUMENTS

| EP | 1048319 | 11/2000 |
| WO | WO 2005/011805 | 2/2005 |
| WO | WO 2008/018067 | 2/2008 |

OTHER PUBLICATIONS

Communication Relating to the Results of the Partial International Search Dated Nov. 27, 2007 From the International Searching Authority Re.: Application No. PCT/IL2007/000983.

(Continued)

*Primary Examiner* — Carl H Layno
*Assistant Examiner* — Brian T Gedeon

(57) ABSTRACT

A multi-contact electrode for neural tissue stimulation is described. The electrode has an axis and includes a plurality of electrodes going along the axis. Each electrode ends with a contact, and at least one of the contacts has an internal edge, resulting in non-uniform electrical properties throughout the contact surface facing the tissue. Also described are methods of making an electrical contact with an internal edge, and methods and systems for characterizing internal edge.

46 Claims, 16 Drawing Sheets

OTHER PUBLICATIONS

International Preliminary Report on Patentability Dated Feb. 19, 2009 From the International Bureau of WIPO Re.: Application No. PCT/IL2007/000983.
Communication Pursuant to Article 94(3) EPC Dated Jun. 5, 2009 From the European Patent Office Re.: Application No. 07790038.9.
International Search Report Dated Feb. 7, 2008 From the International Searching Authority Re.: Application No. PCT/IL2007/000983.
Written Opinion Dated Feb. 7, 2008 From the International Searching Authority Re.: Application No. PCT/IL2007/000983.

* cited by examiner

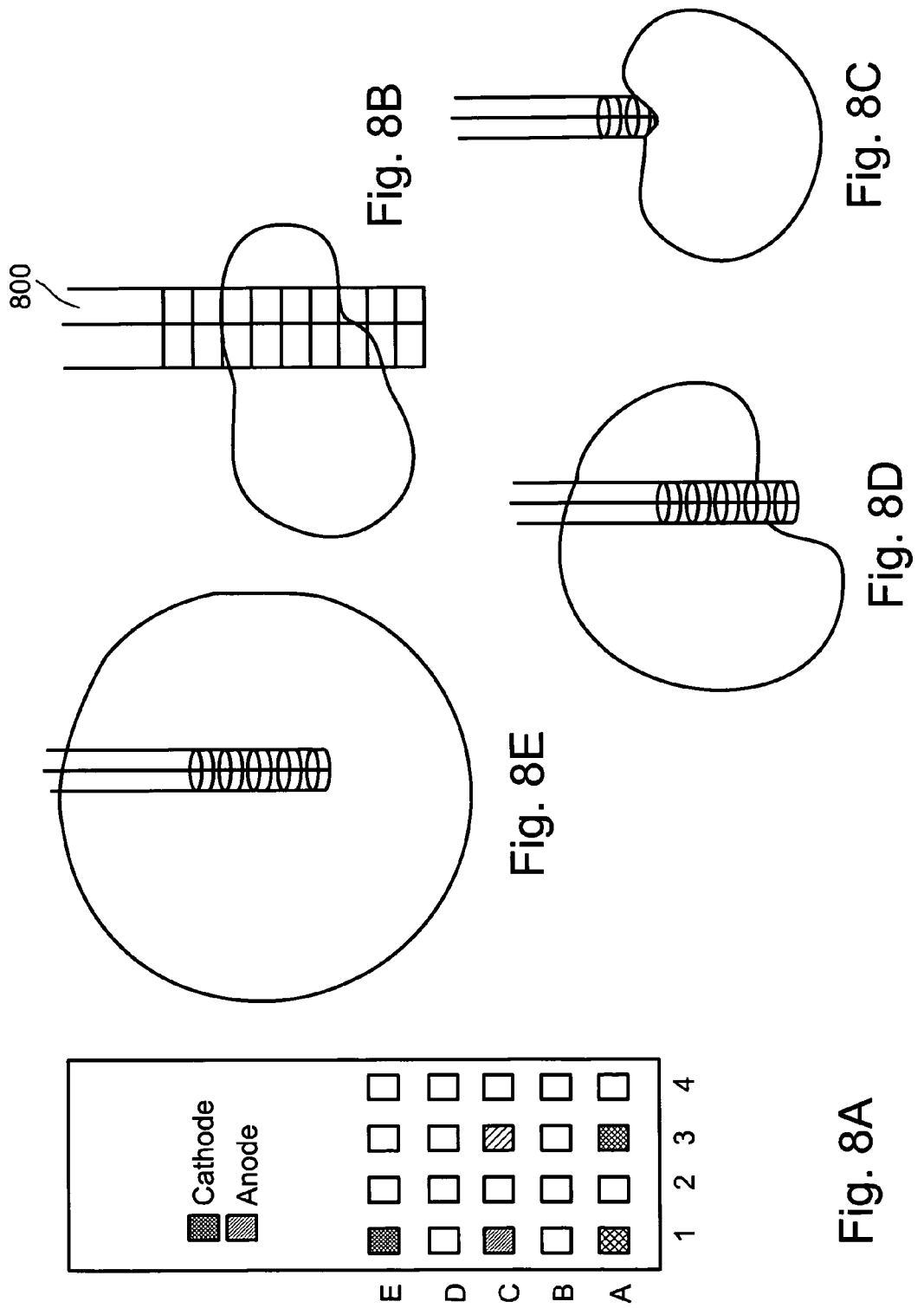

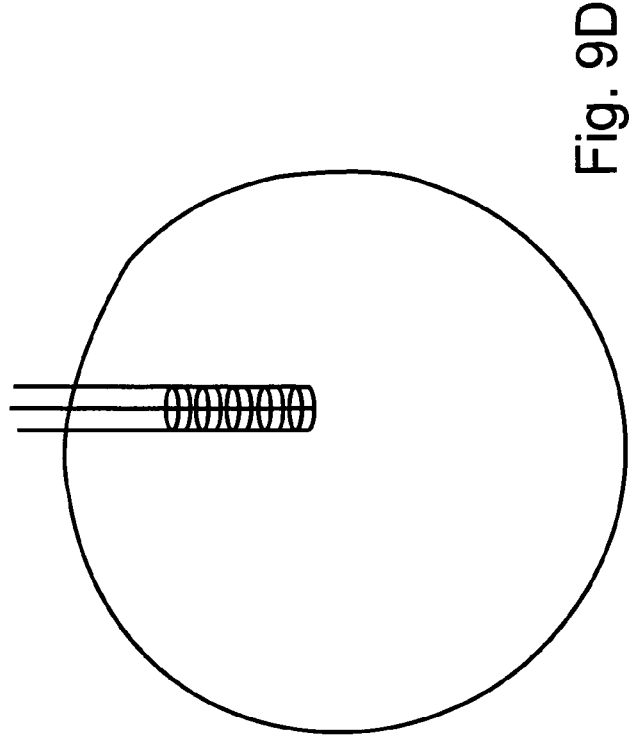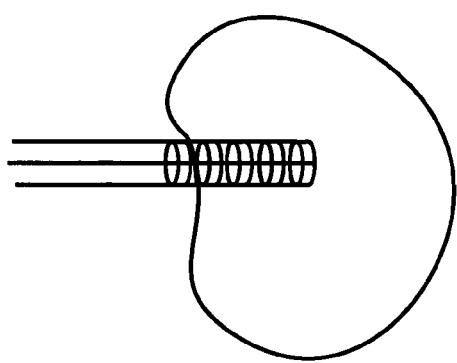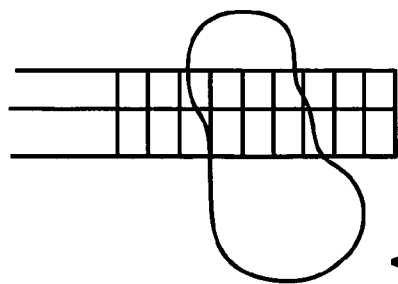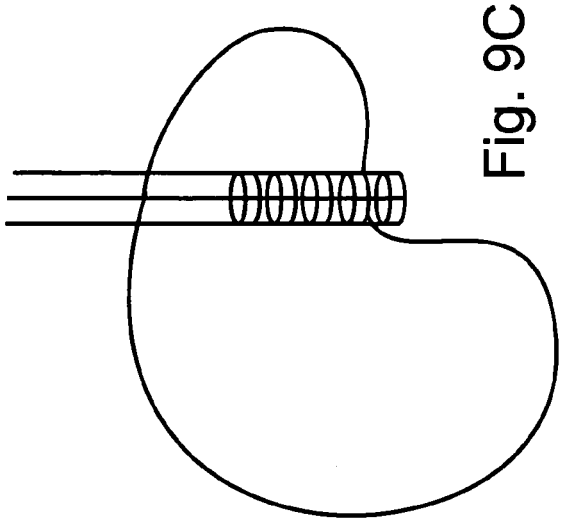
Fig. 9A
Fig. 9B
Fig. 9C
Fig. 9D

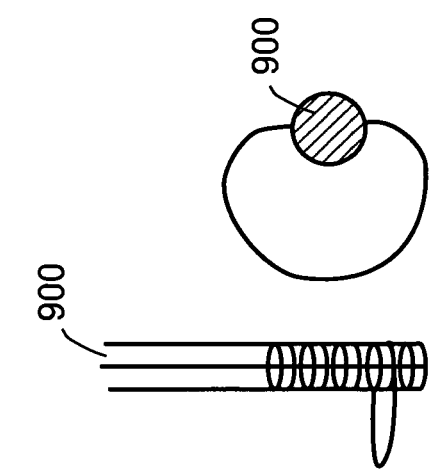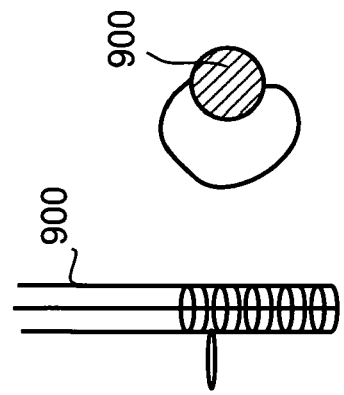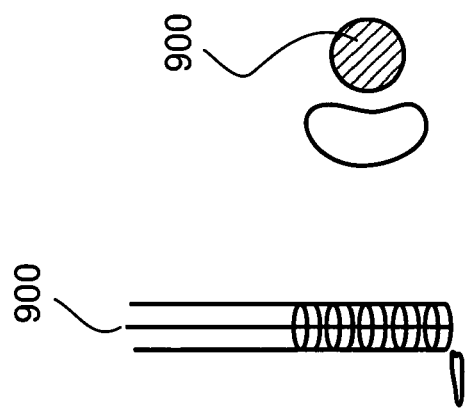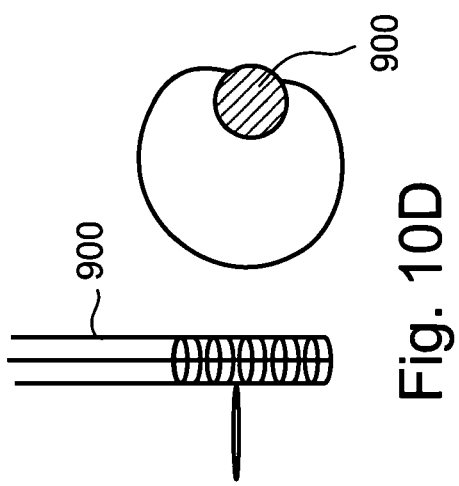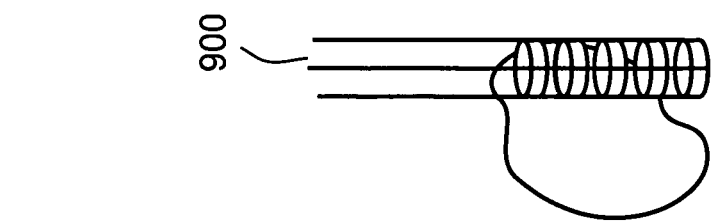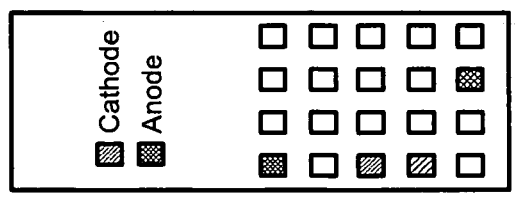

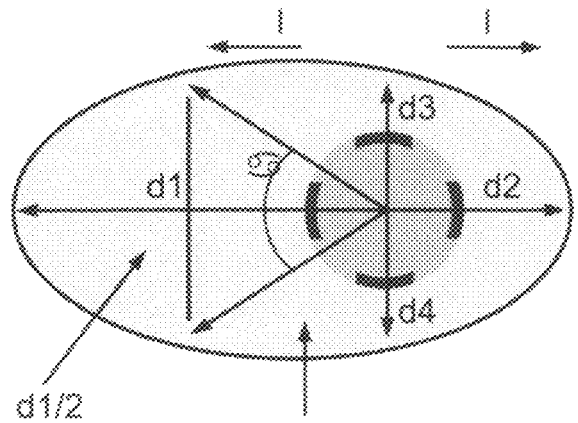
Fig. 10g

Cathodal intensities from high to low — — -
Anodal intensities from high to low ＋ ＋ ＋
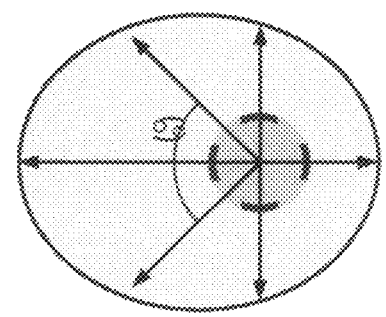
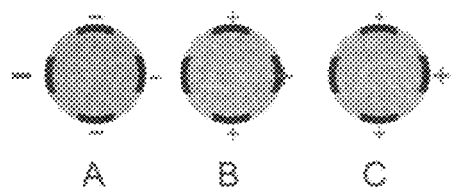
Fig. 10j

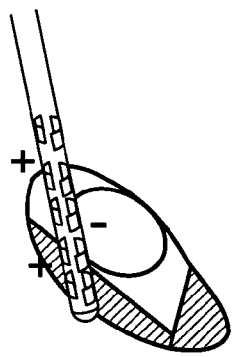
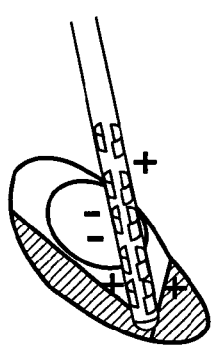
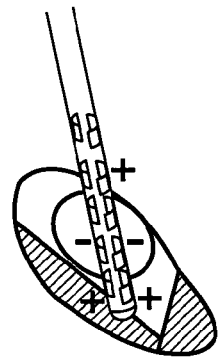
Fig. 11A          Fig. 11B          Fig. 11C
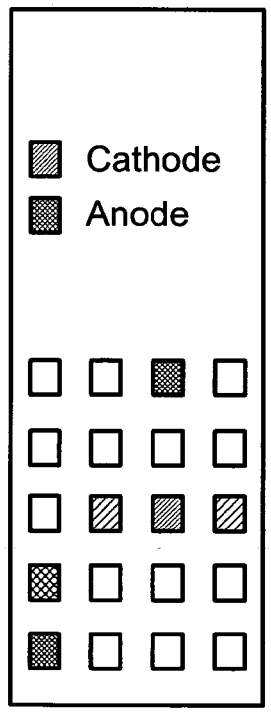
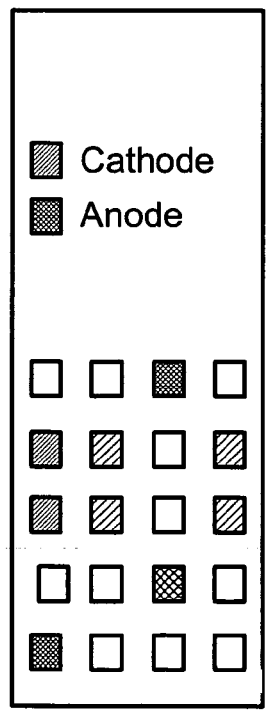
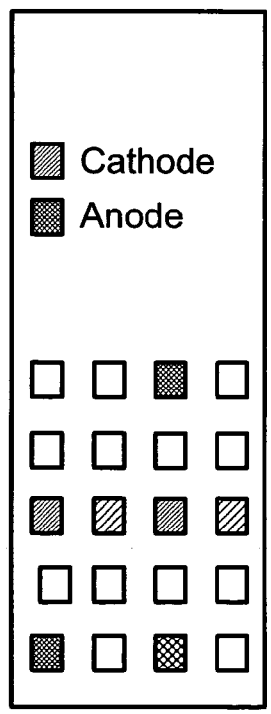
Fig. 11D          Fig. 11E          Fig. 11F

DIRECTIONAL STIMULATION OF NEURAL TISSUE

RELATED APPLICATIONS

This application claims the benefit under 119(e) of U.S. Provisional Patent Applications No. 60/903,533 and 60/903,537 both filed on Feb. 27, 2007.

This application is also a continuation-in-part (CIP) of PCT Patent Application No. PCT/IL2007/000983, filed on Aug. 7, 2007, which claims the benefit of U.S. Provisional Patent Application Nos. 60/903,533 and 60/903,537, both filed on Feb. 27, 2007, 60/849,468 filed on Oct. 5, 2006; 60/835,881 filed on Aug. 7, 2006; 60/835,890 filed on Aug. 7, 2006; 60/835,891 filed on Aug. 7, 2006; and 60/835,902 filed on Aug. 7, 2006.

The contents of each of the above applications are incorporated herein by reference.

FIELD OF THE INVENTION

The present invention relates to electrodes for stimulating tissue at a region of interest and to a method of operating such electrodes.

BACKGROUND OF THE INVENTION

Electric stimulation of neural tissue is used to treat a variety of disorders. Specifically, leadable electric stimulators and leads have been used to treat chronic pain, muscular disorders, hearing problems, symptoms of Parkinson's Disease, bladder control, and sexual dysfunction, among others. Often, a lead terminating in electrodes is situated close to region of interest, the stimulation of which is expected to alleviate the condition of the patient, in a tissue such as spinal cord, nerve roots, muscles, or brain tissue. A leaded signal generator (IPG) connected to the lead is then used to generate patterns of electric pulses that stimulate the tissue.

However, the applied stimulation might also affect tissue at the proximity of the region of interest, and such stimulation might cause unwanted side-effects.

U.S. Pat. No. 7,047,084, the contents of which are incorporated herein by reference, describes an apparatus for providing controlled and directional stimulation patterns for tissue stimulation. The apparatus includes a leadable pulse generator connected to a lead. The lead has electrodes placed about a perimeter. In addition, the lead may include electrodes placed longitudinally along the axis of the lead. This patent suggests that by applying charge differences between circumferentially distributed electrodes, a smaller stimulation field may be established. In addition, the patent suggests that by stimulating between electrodes distributed longitudinally on the same side of a lead, a directional flow field may be established.

U.S. Pat. No. 5,895,416, the contents of which are incorporated herein by reference, describes an electric field steering assembly. The assembly comprises a pulse generator coupled to at least one leaded lead. The lead has at its distal end at least three spaced apart electrodes, and electrical circuitry for adjusting the current and/or voltage at each electrode.

U.S. Pat. No. 6,988,006 discusses creating and steering a supra-threshold stimulation by controlling a time-delay between two sub-threshold stimulations, such that the two stimulations overlap to provide supra-threshold stimulation and changing the time-delay changes the location of the supra-threshold stimulation.

SUMMARY OF THE INVENTION

A broad aspect of some embodiments of the invention concerns operating a lead designed for directionally stimulating neural tissue. The operation comprises providing to anodes and cathodes on the lead unbalanced currents, such that a net flow of current occurs, and sometimes collecting this net flow of current by an electrode residing far (e.g., at a distance at least 5 or 10 times the main dimension of target tissue) from the anodes and cathodes.

The lead is optionally configured for deep brain stimulation, spinal chord stimulation, and/or vagus nerve stimulation.

In an exemplary embodiment of the invention, the net flow is anodal, while local flow is cathodal, so that local tissue can be stimulated using cathodal stimulation, while remote tissue is affected by the less-stimulating anodal flow. Optionally, the fields are arranged so that desired ROIs feel cathodal flow. Optionally or alternatively, areas where stimulation is not desired feel anodal flow.

In an exemplary embodiment of the invention, the fields are controlled by surrounding a cathode or multi-polar stimulation electrode set with a plurality of anodal electrode(s) and modifying the stimulation area by varying the electrification of the electrodes.

In an exemplary embodiment of the invention, anodal fields are used to limit the extent of the stimulation area. In an exemplary embodiment of the invention, cathodal spread is stopped after 5-10 mm. These distances may be useful for reducing the induction of side effects during stimulation.

An aspect of some embodiments of the invention concerns electrodes for neural stimulation that are configured to provide stimulation which is focused mainly at a region of interest, and is preferably effective only at the region of interest.

One example of a focused stimulation field is a field having values above the activation threshold at an ellipsoidal or semi-ellipsoid volume. Optionally, the ellipsoidal volume is more extended at one side of the lead than on another side of the lead. Optionally, the ellipsoidal volume has its longitudinal axis perpendicular to the longitudinal axis of the lead. Optionally, the ellipsoidal volume is non-perpendicular to the longitudinal axis of the lead.

Another example of a focused stimulation field is a field having values above the activation threshold at two ellipsoidal volumes. Optionally, the two ellipsoidal volumes do not overlap. Optionally, the two ellipsoidal volumes have each a longitudinal axis, and the two longitudinal axes are inclined to each other.

Many other examples of focused stimulation fields exist, and are all within the scope of the present invention.

In an exemplary embodiment of the invention there is provided a system for neural stimulation that includes two leads: one lead is leaded at or near the region of interest and includes two groups of electrodes: at least two stimulating electrodes for providing multi-polar (e.g., bipolar, tripolar, quadro-polar, or more) stimulation to the region of interest, and at least one shielding electrode for providing anodal currents. The other lead (e.g., a distant electrode implanted elsewhere in the body, sometimes the IPG case) has a cathode for collecting the anodal currents provided by the shielding electrode(s).

In operation, the stimulating electrodes stimulate the region of interest, and the shielding electrode, electrically coupled to the cathode on the second lead, creates an anodal shield, protecting regions away of the lead from stimulation applied by the stimulating electrodes.

In another embodiment, there is no anode dedicated to the shielding. Instead, the stimulating electrodes on the first lead are electrified such that some of them are anodes and some of them are cathodes, with higher currents loaded on the anodes, so that from a relatively distant point, the total effect is that of an anode. The excess anodal currents created this way are collected by the cathode of the second lead (or a distant electrode or an IPG case), and create anodal shielding.

In another embodiment, only one lead is used, having anodes and cathodes spatially arranged such that under specific electrification conditions the lead creates a stimulation field of a predetermined shape and size. For instance, a lead according to this embodiment may have one group of cathodes (having at lease one cathode) at the vicinity of the region of interest, one group of anodes (having at least one anode) proximally to the cathode(s) and one group of anodes (having at least one anode) distally to the cathode(s). The electrodes are optionally electrified such that the anodes limit the region at which the cathodes provide effective neural stimulation. The arrangement of distal and proximal may be reversed, however, there is usually a desire to limit the distal penetration of a lead into the body, causing the stimulation electrodes to be near the distal end of the lead.

Optionally, the latter embodiment is combined with anodal shielding, utilizing two leads. The anodes on the first lead limit the region at which the cathodes provide effective neural stimulation, and additionally, excess anodal currents are collected by a cathode on the second lead to further shape the electric field created by the system and/or to stop the cathodal spread to distant areas where stimulation is not desired.

Generally, it may be preferable to use leads, where all the electrodes are provided inside an insulating casing, optionally, a casing of cylindrical shape, and each electrode has an electrode contact configured to provide electric currents outside the insulating casing.

In an exemplary embodiment of the invention, the electrode contacts are provided at the perimeter of the casing, forming arranged rows, columns, helixes, or the like. Optionally, each contact follows the outer contour of the casing.

Focused stimulation is optionally achieved by using a plurality of electrode contacts, and enlarging the effective distance between them. One way of enlarging the effective distance between two electrode contacts is shaping the electrode contacts to have internal edges, such that the effective distance between the contacts is the distance between the internal edges.

It has been found by the inventors, that making one, some, or all of the electrode contacts with internal edges may add to the flexibility in defining the shape of the electrical field provided by leads or systems according to some embodiments of the invention. In the present application, the term internal edge is used to refer to any feature that results in non-uniform electrical properties throughout the contact surface facing the tissue. Examples to electrical properties that are non-uniform include impedance per surface area, and current flux. In this context, internal edge is a structural feature that behaves electrically as an edge, but is not at the edge of the contact, but rather on an internal part thereof. Optionally, an internal edge comprises a plurality of mini internal edges. Optionally, the plurality of mini internal edges has a uniform density. Alternatively, the mini internal edges are disposed to create regions of different mini edge densities. For example, an internal edge may comprise several mini internal edges, the concentration profile of which has a maximum at the center of the internal edge.

Small electrode contacts, as suggested for use in some embodiments of the invention, have higher impedance than large contacts as typically used in the prior art. In an exemplary embodiment of the invention, supplying current of a defined intensity with a small contact is facilitated by using higher voltage than in the prior art. According to exemplary embodiments of the invention, the voltage difference between coupled electrodes in a lead is between about 10V to about 50V, optionally between about 15V and 20V. Optionally, multiple voltages are provided, for example, 3, 5, 10, 20 or intermediate numbers of different voltages. Optionally, the voltages are set using current sources, of which several may be provided, for example, 2, 3, 5 or greater or intermediate numbers.

In an embodiment of the invention, the internal edges of the various contacts are arranged in systematic order on the outer surface of the multi-contact electrode. For, example, the various internal contacts may be so arranged as to have a pair of internal edges facing each other, four or more internal edges on the same plane, etc. The systematic order may be beneficial for evaluating electrification fields created around the multi-contact electrode when some of the contacts are electrified.

An aspect of some embodiments of the invention concerns a method of making an electrode contact with an internal edge. In one embodiment, the method comprises smoothing the contact before forming the internal edge. The internal edge may be formed, for instance, by roughening, grooving, drilling, wet etching, and/or laser etching.

In some embodiments of the invention, after internal edges are formed, the electrode contacts carrying them are characterized to ensure that the obtained internal contact has around it the desired field distribution. This is optionally a predefined distribution, a distribution similar to that around a reference internal edge, and/or a distribution similar to that around other contacts in the same electrode.

Optionally, the characterization comprises evaluating the electric current, voltage, or charge at various positions around the internal edge. In some embodiments, a system is provided with a holder for a tested contact and a plurality of testing contacts at fixed positions around the holder. Each testing contact is connected to a meter measuring the current, voltage, and/or charge at the testing contact position. This way, each electrode contact placed at the holder may be characterized by values measured at the same positions, and comparison of different contacts may be facilitated. Such characterization method and/or system is optionally useful for characterizing electrode contacts that have, or should have, no internal edges, for example, to obtain indication of the presence of undesired internal edges or other faults in the contact.

An aspect of some embodiments of the invention concerns electrifying contacts of a multi-contact electrode with a smaller number of current sources. In an embodiment of the invention, a sequence of pulses is provided such that one current source electrifies two or more contacts sequentially, within short enough a period, such that the tissue is stimulated as if the different pulses were provided simultaneously.

In some embodiments, an electrification scheme is first provided, and then, different electrodes are loaded with portions of the total current assigned to them in the electrification scheme, such that the total current provided in each pulse is zero, or some other predetermined current, and the total current provided in all the pulses together to each of the electrodes is the same as assigned to the same electrode in the electrification scheme.

An aspect of some embodiments of the invention concerns a method of designing an electrification scheme for a multi-contact electrode, so as to stimulate a region of interest (ROI).

In an embodiment of the invention, a region of interest is defined, and an initial electrification scheme is suggested, for instance, by guessing. Then, the field provided by the multi-contact electrode, if electrified using the suggested electrification scheme is calculated, and compared to the region of interest. If the comparison is not satisfactory, an optimization is run, for changing the suggested electrification scheme into one that provides a satisfactory compatibility between the region of interest and the region that is expected to be electrified by the electrification scheme.

Optionally, the field is calculated in a crude approximation, according to which each contact is a single point charge source. Optionally, each contact is approximated by a small number of point charge sources, for instance, 2, 3, 4, or 5.

Optionally, the compatibility between the region of interest and the stimulated region comprises comparison between some central characteristics of each of the fields. Such characteristics may be, for example, the position of the center of the field, the angle between an axis of the filed and the axis of the multi-contact electrode, and/or the size of the two fields.

There is thus provided in accordance with an embodiment of the invention a multi-contact electrode for neural tissue stimulation having an axis and comprising a plurality of electrodes going along said axis, each electrode ending with a contact, wherein at least one of said contacts has an internal edge.

Optionally, the multi-contact electrode is configured for deep brain stimulation.

Optionally, the multi contact electrode comprises a plurality of internal edges arranged in a systematic order on an outer surface of the multi contact electrode.

In exemplary embodiments of the invention, the systematic order comprises at least one of the following:

(a) having a pair of opposing contacts with the internal edges arranged such that a line connecting the centers of the internal edges intersects the axis of the multi-contact electrode;

(b) having three contacts, each with an internal edge, and the three internal edges having their centers on a plane that is perpendicular to said axis;

(c) having four contacts, each with an internal edge, and the centers of the four internal edges are on the same plane;

(d) having centers of internal edges arranged along a helix;

(e) having contacts, each with a linear internal edge parallel to said axis.

Optionally, the systematic order comprises a pair of opposing contacts with the internal edges arranged such that a line connecting the centers of the internal edges intersects the axis of the multi-contact electrode.

Optionally, said line is perpendicular to said axis.

Optionally, said systematic order comprises having three contacts, each with an internal edge, and the three internal edges having their centers on a plane perpendicular to said axis.

Optionally, the multi-contact electrode has four contacts, each with an internal edge; and the centers of the four internal edges are on the same plane.

Optionally, said systematic order comprises centers of internal edges arranged along a helix.

Optionally, said helix is of a uniform density.

In an exemplary embodiment the current density at the internal edge on a contact is larger than the current density at the same contact away of said internal edge, in a factor of 10 or less.

In an exemplary embodiment, the multi-contact electrode comprises contacts shaped as a sector of a circular cylinder and having an internal edge.

Optionally, the multi-contact electrode has a recessed electrode contact.

Optionally, an internal edge in an electrode contact comprises a protrusion.

Optionally, an internal edge in an electrode contact comprises a plurality of recesses.

Optionally, the multi-contact electrode has a recessed periphery, and the plurality of recesses are of larger density at the center of the internal edge than at said recessed periphery.

Optionally, said density gradually increases from said periphery to said center.

Optionally, at least one of said internal edges comprises a round recess.

Optionally, one or more of said internal edges has a vertex, optionally, said vertex is smooth.

Optionally one or more of the internal edges is triangular.

Optionally, one or more of said internal edges has one or more curved side.

Optionally, one or more of said internal edges comprises a groove.

Optionally, the contacts are arranged in 5 rows.

Optionally, at least 50% of the contacts comprises an internal edge.

Optionally, at least 90% of the contacts comprises an internal edge.

In an exemplary embodiment, the multi-contact electrode is packaged in a sterile packaging.

In accordance with an exemplary embodiment of the invention, there is provided a method of producing an electrode contact with an internal edge comprising:

(a) providing an electrode contact free of internal edges; and (b) shaping, optionally, according to a plan, the electrode contact to have an internal edge.

In an exemplary embodiment, providing an electrode contact free of internal edges comprises:

providing an electrode contact; and smoothing the electrode contact so as to obtain an electrode contact free of internal edges.

Optionally, shaping includes roughening a portion of the electrode contact.

Optionally shaping comprises grooving the electrode contact.

Optionally, shaping comprises drilling, optionally laser drilling, at least one recess in said contact.

Optionally, shaping comprises electrical etching.

There is also provided by an exemplary embodiment of the invention a method of evaluating quality of an examined electrode contact comprising:

providing a reference electric current distribution around an electrode contact to obtain a standard current distribution;

measuring electric current distribution around said examined electrode contact to obtain an examined current distribution; and evaluating quality of the examined electrode contact responsive to similarity between said desired and said examined current distributions, wherein larger similarity is evaluated as higher quality.

In some embodiments, providing a reference electric current distribution comprises measuring said reference electric current distribution.

In an exemplary embodiment, measuring electric current distribution around an electrode contact comprises:

creating a potential difference between said electrode contact and a plurality of examining electrodes, such that said electrode contact is at a first electric potential and each of said examining electrodes is at a second electric potential; and measuring the electrical current flowing in each of said plurality of examining electrodes.

In accordance with a further embodiments of the invention there is provided a method of improving quality of an electrode contact, the method comprising:

evaluating said quality using a method according to claim 36; and thereafter, without displacing the electrode contact in relation to the examining contacts, electrically etching said electrode contact so as to improve said quality.

In accordance with an embodiment of the invention there is provided a system for evaluating quality of electrode contacts comprising:

a bath with a conducting solution a fixing member, configured for fixing an electrode contact;

a power source, configured for connecting with one pole to an electrode contact fixed by said fixing member;

a plurality of electrodes, positioned around said fixing member, connected to a second pole of said power source and separated from said electrode contact by said conducting solution; and a plurality of current meters configured to measure currents flowing at each of said plurality of electrodes.

Optionally, evaluating and electrically etching comprises using a system as described above.

There is also provided in accordance with an exemplary embodiment of their invention a method of operating a neural tissue stimulation system comprising electrodes and a number of current sources, the method comprising:

defining a number of active electrodes to be electrified, the number of active electrodes being larger than the number of current sources;

associating a current with each active electrode;

dividing a current associated with an active electrode to two or more current portions; and electrifying said active electrode with a sequence of two or more pulses, each carrying one of said current portions.

Optionally, in each of said at least two pulses the total current, with which all the active electrodes are electrified, is equal to the sum of currents associated with all the active electrodes.

Optionally, the total current provided by all the active electrodes in each pulse of said sequence of pulses is zero.

Optionally, at least one of said current sources is associated with a collecting electrode.

Optionally, electrifying sequentially comprises electrifying a single electrode at least once with a first current source and, thereafter, at least once with a second current source, different from said first current source.

Optionally, in each pulse, all the active electrodes, electrified in said each pulse, are simultaneously electrified.

There is also provided in accordance with an exemplary embodiment of the invention a method of operating a neural tissue stimulation system comprising:

defining an electrification scheme comprising:
a number of active electrodes to be electrified; and
currents, each to be delivered by each of the active electrodes, the sum of said currents defining a total current;
providing an electrification sequence, defining a pulse sequence, wherein in each pulse of said sequence a number of electrodes is electrified with a current portion, such that:
in each pulse the total current provided by all the electrodes is equal to said total current; and
in the entire sequence each electrode is electrified with a current as defined thereto in the electrification scheme.

In some embodiments, the number of active electrodes is larger than a number of current sources available to the system, and wherein the number of electrodes electrified in each pulse is not larger than the number of available current sources.

Optionally, in each pulse of said sequence a number of electrodes is simultaneously electrified with a current portion.

There is also provided in accordance with an exemplary embodiment of the invention, a neural tissue stimulation system comprising:

a multi contact electrode comprising a plurality of electrode wires, each ending with an electrode contact;

at least two current sources, operable to electrify said plurality of electrode contacts, said second number being smaller than said first number; and a controller, configured to:
receive an electrification scheme comprising instructions to electrify active electrodes, the number of which is larger than the number of current sources; and
control each current source to sequentially electrify one or more of the active electrodes, such that when the electrodes are in a neural tissue, the neural tissue is stimulated as if the active electrodes were electrified simultaneously in accordance with said electrification scheme.

Optionally, the system comprises a current collecting electrode.

Optionally, the current collecting electrode comprises an additional electrode, configured to be positioned away of said multi contact electrode.

Optionally, the current collecting electrode is an intermediate contact integral with said multi contact electrode.

There is also provided in accordance with an exemplary embodiment of the invention, a method of stimulating electrically excitable tissue with a multi contact electrode having an axis and comprising a plurality of electrodes going along said axis, each electrode ending with a contact, said multi contact electrode implanted in the vicinity of the tissue, the method comprising:

(a) defining a desired electrical field to be generated by said multi contact electrode, said desired electrical field having borders beyond which the desired electrical field is below a threshold value;

(b) suggesting a first electrification scheme comprising active electrodes to be electrified and current associated with each active electrode;

(c) calculating a calculated electrical field expected to be generated around the multi contact electrode if the multi contact electrode is electrified in accordance with the first electrification scheme;

(d) calculating a first compatibility function between the calculated field and the desired field, said calculating is in response to a plurality of compatibility parameters;

(e) amending said first electrification scheme so as to obtain a second electrification scheme, having a better compatibility function; and (f) doing at least one of:
storing the optimized electrification scheme on a computer storage;
displaying an image indicative of the optimized electrification scheme; and
electrifying electrodes of the multi contact electrodes in accordance with the optimized electrification scheme,
wherein calculating an electrical field comprises calculating as if each contact of the multi contact electrode consists of 5 or less point charges.

Optionally, one of said compatibility parameters is responsive to a distance between a center of the calculated field and the center of the defined field.

Optionally, one of said compatibility parameters is responsive to an angle between an axis of the calculated field and an axis of the defined field.

Optionally, one of said compatibility parameters is responsive to a difference between the size of the calculated field and the size of the defined field.

Optionally, defining an electrical field comprises:
defining a volume within said borders, and
defining a field direction preferred at said volume and
one of said compatibility parameters is an angle between the preferred field direction and the direction of the calculated field at said volume.

Optionally, calculating a compatibility function comprises calculating an average of said plurality of compatibility parameters.

Optionally, the average is weighted such that different compatibility parameters have different weights.

In some embodiments, amending said first electrification scheme so as to obtain a second electrification scheme comprises iteratively computing compatibility functions of various electrification schemes, and an electrification scheme, the compatibility function of which is computed in one iteration, is defined respective to an electrification scheme and the compatibility function as computed in a former iteration.

There is also provided in accordance with an exemplary embodiment of the invention, a method of stimulating electrically a neural fiber in the brain, with a multi-contact electrode implanted in the brain, the method comprising:

(a) defining a desired electrical field to be generated by said multi contact electrode, said desired electrical field having borders beyond which the desired electrical field is below a threshold value and, within said borders a volume and a field direction preferred at said volume;

(b) suggesting an electrification scheme, comprising active electrodes to be electrified and current associated with each active electrode;

(c) optimizing said suggested electrification scheme in respect of an angle between an axis of an electrical field expected to be generated around the multi contact electrode if the multi contact electrode is electrified in accordance with the electrification scheme and said field direction as to obtain and optimized electrification scheme; and (d) doing at least one of:
storing the optimized electrification scheme on a computer storage;
displaying an image indicative of the optimized electrification scheme; and
electrifying electrodes of the multi contact electrodes in accordance with the optimized electrification scheme.

There is therefore provided in accordance with an exemplary embodiment of the invention, a system for stimulating neural tissue comprising:
at least two electrical contacts configured to deliver a multi-polar stimulation to a region of interest in the vicinity of said contacts;
at least one cathode contact remote from said contacts; and
a signal generator electrically coupled to said contacts and configured to electrify said contacts such that tissue near said cathode contacts is under the influence of anodal flows and is not stimulated.

Optionally, said cathode is configured to collect anodal currents from said at least two electrical contacts.

In an exemplary embodiment of the invention, said near tissue is closer by a factor of 2 to said electrical contacts relative to said cathode contact.

In an exemplary embodiment of the invention, said near tissue is closer by a factor of 4 to said electrical contacts relative to said cathode contact.

In an exemplary embodiment of the invention, said near tissue is closer by a factor of 8 to said electrical contacts relative to said cathode contact.

In an exemplary embodiment of the invention, said contacts and said cathode contact are provided on a single lead.

In an exemplary embodiment of the invention, said cathode contact is mounted on a body of said system.

In an exemplary embodiment of the invention, said system is implantable.

In an exemplary embodiment of the invention, said signal generator is configured to electrify said contacts with at least 2 different voltage magnitudes.

In an exemplary embodiment of the invention, said at least two contacts are configured to apply a bipolar stimulation.

In an exemplary embodiment of the invention, said at least two contacts are provided on a lead including at least 10 electrical contacts.

In an exemplary embodiment of the invention, said lead is sized for electrification of an STN area in a brain for treating Parkinson's disease.

In an exemplary embodiment of the invention, there is substantially no stimulation on one side of a plane tangential to the lead.

In an exemplary embodiment of the invention, said contacts are arranged on said lead in a helical arrangement.

In an exemplary embodiment of the invention, said at least two contacts are provided on a lead including at least one ring contact and at least 4 sectorial contacts.

In an exemplary embodiment of the invention, said at least one of said at least two contacts is provided with at least one internal edge adapted to provide preferential current exit from said edge.

In an exemplary embodiment of the invention, said signal generator is configured as a current source.

In an exemplary embodiment of the invention, said signal generator is configured to provide at least 20 volts to at least one of the contacts.

In an exemplary embodiment of the invention, the system comprises an N×M switch adapted to selectively attach one of N power sources of said signal generator to M contacts including said at least two contacts and said cathode contact.

There is also provided in accordance with an exemplary embodiment of the invention, a system for stimulating neural tissue comprising:
at least one cathodic contact;
at least two anodic contacts on opposite sides of said cathodic contact; and
a signal generator electrically coupled to said contacts and configured to electrify said contacts to selectively stimulate a region of interest adjacent said contacts and configured to selectively steer said region of interest in at least one mode selected from extension/retraction, tilting, shifting and narrowing/widening.

In an exemplary embodiment of the invention, said generator is configured to provide at least two of said modes.

In an exemplary embodiment of the invention, said generator is configured to provide all of said modes.

In an exemplary embodiment of the invention, said generator is configured to provide said modes by modifying current to at least two different contacts, belonging to at least two of said cathodic contact and said two anodic contacts.

In an exemplary embodiment of the invention, the system comprises a remote cathodic contact.

In an exemplary embodiment of the invention, said contacts are mounted on an axial lead and wherein signal generator is configured to generate an ellipsoid-like stimulation area which has a main axis tilted non-perpendicular to said lead axis.

In an exemplary embodiment of the invention, said contacts are mounted on an axial lead and wherein signal generator is configured to generate an ellipsoid-like stimulation area which has a minor axis offset from said lead axis.

There is also provided in accordance with an exemplary embodiment of the invention, a system for stimulating neural tissue comprising:

an axial lead;
at least one cathodic contact on said lead;
at least two anodic contacts on said lead and on opposite sides of said cathodic contact; and
a signal generator electrically coupled to said contacts and configured to electrify said contacts to selectively stimulate a region of interest adjacent said contacts.

There is also provided in accordance with an exemplary embodiment of the invention, a system for stimulating neural tissue comprising:

an axial lead;
at least one cathodic contact on said lead;
at least one anodic contact on said lead; and
a signal generator electrically coupled to said contacts and configured to electrify said contacts to selectively stimulate a region of interest adjacent said contacts, in the form of an ellipsoid-like shape and having no axis co-axial with said lead axis.

In an exemplary embodiment of the invention, said ellipsoid-like shape is tilted relative to said axis.

In an exemplary embodiment of the invention, said ellipsoid-like shape is offset relative to said axis.

In an exemplary embodiment of the invention, there is substantially no stimulation on one side of a plane tangential to the lead.

There is also provided in accordance with an exemplary embodiment of the invention, a method of controlling a lead, comprising:

providing a lead including a plurality of contacts into tissue;
selectively electrifying at least three contacts so that ROI tissue near at least one of said contacts is stimulated by cathodal stimulation; and
controlling said selective electrification so that an anodal flow affects tissue near said ROI tissue and limits an extent of said stimulation.

In an exemplary embodiment of the invention, controlling comprises causing a stimulation by at least two of said contacts to include excess anodal current; and collecting said excess current by a remote cathode.

In an exemplary embodiment of the invention, controlling comprises surrounding said a cathodal contact on at least two sides by anodal contacts.

In an exemplary embodiment of the invention, controlling comprises steering said ROI in at least one of shifting, tilting and ROI size.

BRIEF DESCRIPTION OF THE DRAWINGS

Exemplary embodiments of the invention are herein described, with reference to the accompanying drawings. With specific reference now to the drawings in detail, it is stressed that the particulars shown are by way of example and for purposes of illustrative discussion of some exemplary embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 8A is a schematic illustration of a plan view of a distal end of a lead according to an embodiment of the invention;

FIG. 8B is a cross-section in a plain parallel to the longitudinal axis of lead in a cathodal spread created by activating all the electrodes shown as anodes and cathodes in FIG. 8A;

FIGS. 8C, 8D, and 8E are schematic illustration of cross-sections similar to that of FIG. 8C, with some of the anodes not activated;

FIGS. 9A-9D are schematic illustrations of cross-sections similar to those presented in FIGS. 8B-8E, but with a different location of the current-collecting electrode.

FIGS. 10A-10E illustrate a three-dimensional shape of a cathodal spread created around a distal portion of a lead, when the contacts on the distal portion are electrified as illustrated in the plan view presented in FIG. 10F;

FIG. 10F shows an electrification plan for the spreads shown in FIGS. 10A-10E;

FIG. 10G illustrates various properties of a cathodal spread when applied in accordance with exemplary embodiments of the invention;

FIG. 10H, FIG. 10I and FIG. 10J illustrate various electrification schemes and their effect on the cathodal spread, in accordance with exemplary embodiments of the invention;

FIGS. 11A-11F illustrate how motoric STN may be stimulated with a lead according to exemplary embodiments of the invention.

DESCRIPTION OF EXEMPLARY EMBODIMENTS

Overview

Figure 1:
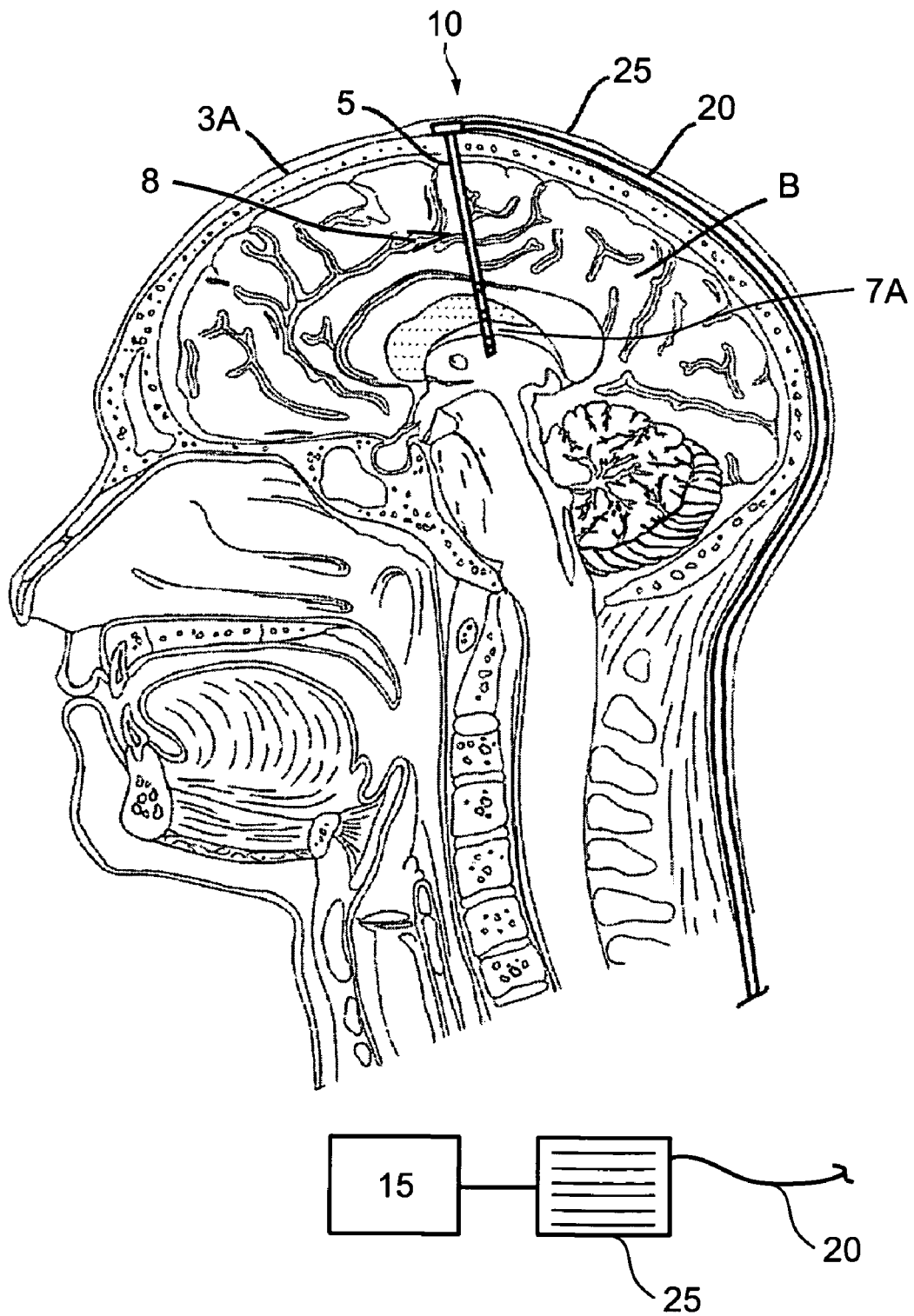
FIG. 1 is a cross-sectional view of the brain showing a lead placed in the brain according to an embodiment of the invention.

A lead according to various embodiments of the invention may be leaded in a brain for supplying therapeutic neural stimulation. FIG. 1 is a cross-sectional view of a brain (B) showing a lead (5) placed in the brain according to an embodiment of the invention. Lead 5 has a distal portion (7) a proximal portion (10), and an intermediate portion (8) between them.

Distal portion 7 of lead 5 is leaded in brain B through a hole in the skull. Distal portion 7 has electrode contacts 7A for providing electrical stimulation to the brain. Such contacts are described in more detail below. In other embodiments of the invention, the electrode contacts may be in other parts of the lead, such as in a proximal portion or in an intermediate portion, all depending on the direction at which the lead is inserted into the tissue. Nevertheless, for simplicity of presentation, the following description uses terminology suitable for a lead inserted as shown in FIG. 1. A skilled person would easily understand how these terms are to be read in case the lead is inserted in a different direction or through a different path.

Proximal portion 10 of lead 5 is shown connected to a power source 15 through a cable (20). Cable 20 connects lead 5 to power source 15 though a leaded pulse generator (IPG) 25, configured to allow connecting each contact 7A either to a positive or to a negative pole of a power source, and to load each contact with a voltage, optionally independently on the voltage loaded on the other contacts. In an exemplary embodiment of the invention, electrode contacts that are not activated are left floating. In an exemplary embodiment of the invention, any electrode contact can be in any of three states: anodal, cathodal or floating. Furthermore, different electrodes can have different relative voltages, even if they have the same polarity. It should be noted that even electrode contacts in a same row and/or column can be different or modified during treatment. In some embodiments, the flexibility is not total and some combinations of electrifications are not supported. Optionally, the electrification uses a switch interconnecting a plurality of current sources and the electrodes. Optionally, a 3×20 switch is used. Exemplary switch types which may be used in some embodiments of the invention include, semiconductor, magnetic and relay switches. Optionally, cable 15 is leaded between the scalp (25) and skull (30). Optionally, IPG 25 is leaded outside the brain, for instance, in the chest.

In an exemplary embodiment of the invention, the IPG includes a memory having stored thereon parameter settings and/or programming. Optionally, the IPG includes circuitry to receive signals from the lead and determine a desirable stimulation (or lack thereof) in response. For example, apparatus as described in PCT publication WO 03/028521, the disclosure of which is incorporated herein by reference, is used.

Exemplary Leads

Generally, leads described in U.S. Pat. No. 7,047,084, incorporated herein by reference, are suitable for use according to the present invention. Alternative leads, optionally with improved features are described below and may be used instead. Alternatively, other multi-contact lead designs are used. A particular usefulness of some embodiments of the invention relates to low diameter cylindrical leads, in which the actual distances between contacts is small. Optionally, the method is used herein are applied to other electrode designs, such as flat electrodes, such as used for brain surface and for spinal surfaces.

Figure 2:
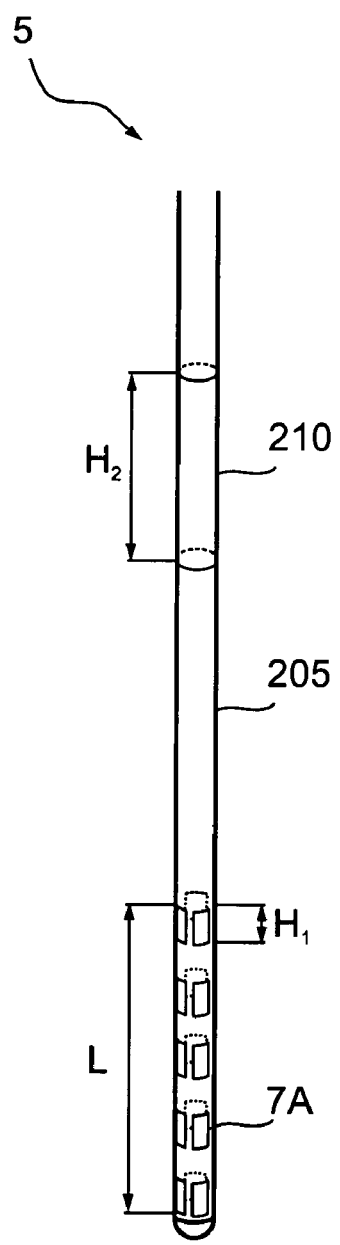
FIG. 2 is a is a schematic illustration of lead according to an embodiment of the invention.

FIG. 2 is a schematic illustration of lead 5 configured for stimulating an STN of a human brain according to an embodiment of the invention. Lead 5 has an insulating casing 205, and electrical conductors running through body 205 from contacts 7A into cable 20 (shown in FIG. 1). The conductors are not shown in the figure for simplicity of representation, but are generally arranged as shown in FIG. 2B or 7 of the above-mentioned U.S. Pat. No. 7,047,084.

Proximally to contacts 7A there is shown an intermediate contact 210. Intermediate contact 210 is shown to be cylindrical, but in other embodiments, may have any shape similar to that contacts 7A are described herein to optionally have. However, as in some embodiments it may be preferable that an intermediate contact such as contact 210 does not stimulate tissue in its vicinity, at least in these embodiments an intermediate contact has a larger surface area than distal contacts, such that currents flowing from the intermediate contact are small enough not to stimulate tissue at their vicinity.

Preferably, lead 5 is leaded in the neural tissue, such that contacts 7A are in the vicinity of the ROI, and intermediate contact 210 contacts regions that has a low concentration of brain cells or fibers, such that electrifying the intermediate contact does not stimulate tissue in its vicinity, or at most, stimulates it to an insignificant extent. Optionally, intermediate contact 210 is utilized as a shielding anode.

Details of a lead structure may be tailored for different applications. For instance, the lead shown in FIG. 2 is designed specifically for stimulating the STN of a human brain. The inventors found that for this application it is preferable to have a lead with five rows of contacts, four contacts in each raw. Each contact has a height H1 of about 1-1.5 mm, and distributed longitudinally such that the length L between the distal edge of the most distal contact and the proximal edge of the most proximal contact is about 9-12 mm.

Intermediate contact 210 is optionally a cylindrical surface having a height H2 of about 6-12 mm, for example, 10 mm.

Figure 3A:
FIGS. 3A and 3B are schematic illustrations of leads having helically arranged contacts according to exemplary embodiments of the invention.
Figure 3B:
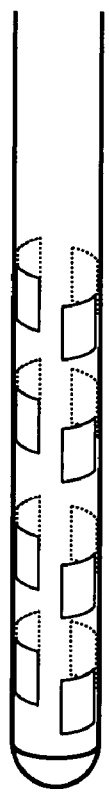

FIGS. 3A and 3B are schematic illustrations of leads having helically arranged contacts according to exemplary embodiments of the invention. In general, a helical or semi helical design can give a contacts spread that is similar to non-helical, with reduced resolution in some cases. Potential advantages which may be realized with helical designs are: results close to what is needed, using fewer current sources. In some cases the planes defined by activating opposite contacts can yield better optimized stimulation to targeted tissue, for example tissue aligned perpendicularly to these planes. Helical design can allow contacts sitting on a same row more distant in the plane perpendicular to the lead axis. Helical design can assist in manufacture, by naturally offsetting the electrical attachment to the contacts.

In FIG. 3A, all the contacts are evenly distributed in a helical form, forming a helix of uniform density. The displacement between centers of adjacent contacts along the MCE axis is optionally about 0.3-0.9 mm, for example, 0.75 mm.

In FIG. 3B the contacts are arranged in rows, and each row of contacts is distributed evenly in a helical form, forming a helix with non-uniform density. The displacement between centers of adjacent contacts along the MCE axis in the same row is between 0.1-0.3 mm while the distance between the rows is 0.5 mm to 1 mm.

In an exemplary embodiment of the invention, the lead is made of a rigid part, including the distal portion and optionally also the intermediate portion, and a flexible part, comprising the proximal portion, and optionally also the intermediate portion. Optionally, the rigid part is 10-15 mm long, and the intermediate part is 1-10 mm long. The lead is optionally made of a light-weight biocompatible material, for instance a plastic or other polymer. The electrodes are optionally made of small diameter wires, for example, micro wires, coated with a flexible biocompatible material. The rigid part allows the electrode to be inserted in a guide tube, and also allows connecting the rigid part to a cable, which is optionally extending to the IPG (leaded pulse generator), in the chest, head, or any other part of the body as known in the art per se. An electrode with a rigid distal portion and a flexible proximal portion is suitable for implantation in the brain (mainly for deep structure in the brain) for deep brain stimulation (BBS) and are also useful for implantation on the spinal chord for spinal cord stimulation (SCS). The lead is described herein mainly in the context of stimulation, nevertheless, it is also useful for recording neural signals, or other biologically produced electrical signals.

Optionally, the electrode comprises 8 rings, each comprising four contacts. Optionally, each of the contacts covers an arc of a little less than a quarter of a circle, such that every 4 contacts form together a ring, and can mimic one ring electrode. Other numbers of rows can be used, for example, 4, 6, 10 or 12. Optionally or alternatively, other numbers of contacts can be used, for example, 3, 5, 6, 7, 10 or intermediate or greater numbers.

Exemplary Lead Manufacture

In preparation of the lead, the contacts are optionally connected to the microwires, and arranged in a mold, optionally an insulating mold, made of biocompatible dielectric material. Then, an insulating biocompatible material, for instance Polyurethane in liquid state is molded into the mold, and solidifies. The outer mold optionally functions as a casing for the lead. At this stage, the contacts are optionally shaped to have their final form, for instance, arcs, following the outer surface of the casing. The flexible connector is optionally produced in a similar manner, but from a more flexible material.

Figure 4:
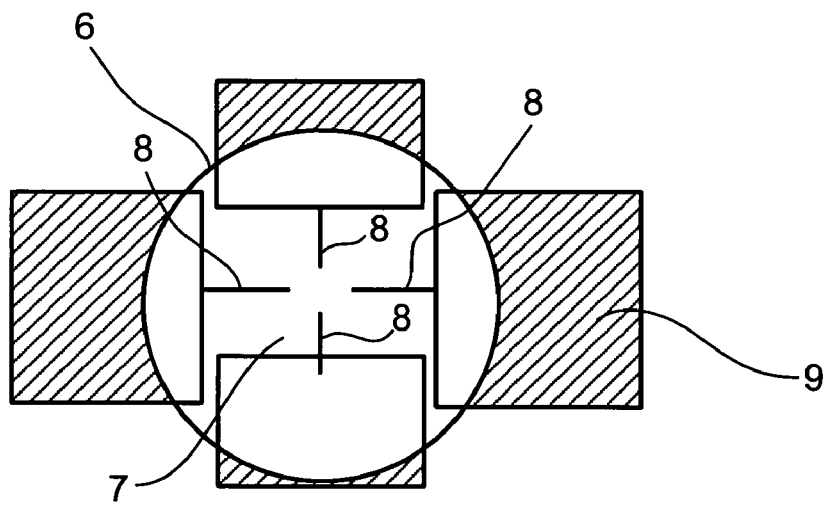
FIG. 4 is a schematic illustration of a cross-section in a lead at preparation, before the contacts are shaped to have their final form, according to an exemplary embodiment of the invention.

FIG. 4 is a schematic illustration of a cross-section in a lead at preparation, before the contacts are shaped to have their final form. Shown in the figure are contacts (9) connected to wires (8). The contacts optionally protrude from a solid molded body (7), which is given within a casing (6). At the final shaping, the protruding parts (shaded) are optionally removed, such that the contacts' faces follow the outer contour of the casing.

Shapes of Exemplary Contacts

In exemplary embodiments of the invention at least one of the contacts of the lead has an internal edge. The current going through the internal edge is generally much larger than the current going through the other parts of the contacts, and therefore, electrically, the effective distance between contacts with internal edges is larger than that between the same contacts but without the internal edge.

An internal edge is a region, away of the edge of the contact, optionally at the center of the contact, that electrically behaves similar to an edge, namely, allows accumulation of large current density. An internal edge creates near it a hot spot, which the state of the art considers to be unwanted. However, according to exemplary embodiments of the present invention an internal edge is designed not to become so hot as to cause thermal damage to tissue.

In an embodiment of the invention, the size and shape of the internal edge is decided by thermal testing. For instance, an internal edge is created in a contact, and then a voltage is loaded on the contact and temperature development is monitored. If the temperature raises more quickly than some predetermined threshold, the internal edge is smoothed, and testing is repeated to ensure acceptable heating of the contact. Another possible way of testing is by simulation of electrical and heat dissipation due to electrodes activation.

It has been found by the inventors that an electrode contact with properly designed internal edges creates around the contact an electric field that is more directional than that created around smooth contacts. Therefore, contacts with internal edges allow stimulating smaller ROIs, without harmfully stimulating adjacent tissues.

In exemplary embodiments of the invention, a lead is designed with contacts that have internal edges of different kinds, thus widening the possibilities of obtaining different shapes of stimulation fields. For example, some contacts may have an internal edge and some be free of internal edges.

Generally, the internal edge should have current density that is about 2 to about 10 times larger than that of the rest of the contact (e.g., smooth surface thereof), but without reaching damaging values. The current density at the internal edge is preferably less than 30 $\mu C/cm^2$ for monophasic stimulation. For biphasic, the density may be, for example, larger by a factor of, for example, 5, 10, 20, 50 or intermediate amounts. Optionally, a separate phase for recharging is used to overcome a calculated accumulated charge (e.g., based on the tissue interface capacitance.

A contact with an internal edge optionally has an impedance of at least about 500 ohm preferably at least 1000 ohm, and more preferably more than about 1,500 ohm. The impedance is optionally less than about 4000 ohm, preferably less than 3,000 ohm, and most preferably below 2500 ohm. It may be, for example, as high as 5,000 ohm, 10,000 ohm or 20,000 Ohm or intermediate values.

An internal edge is optionally of the length of about ⅓-¼ of the length of the entire contact. Internal edges of shorter5 or longer lengths are also optional. Optionally, the length of the internal edge is the same as the length of the contact In some embodiments, multiple internal edges are provided in a contact. Optionally or alternatively, at least one internal edge is a point protrusion. Optionally or alternatively, at least one internal edge is a line ridge.

For example, with a lead having a diameter of about 1.3 mm the circumference is about 4 mm, and when having four contacts, each contact covers about ¼ of the circumference and has a width of about 1 mm, the internal edge is at the central 0.25-0.4 mm.

In exemplary embodiments of the invention, the internal edges on lead's contacts are aligned in parallel with the axis of the lead. The contact height, parallel to the MCE axis is optionally from about 1 mm to about 1.5 mm.

FIGS. 5A-5E are shapes of exemplary contacts with internal edges. The internal edges are marked with arrows pointing at them.

Figure 5A:
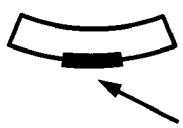
FIGS. 5A-5F are shapes of exemplary contacts with internal edges according to exemplary embodiments of the invention.

In FIG. 5A the internal edge comprises a rough surface, which in fact includes many macroscopic and/or microscopic edges. Optionally, the roughness is selected to achieve the desirable current density ratios. Roughness may be applied to a contact portion by many different means, known in the art per se, for instance, sand paper, pulsed moving laser, laser drilling (for example, laser percussion drilling) and TiN (titanium nitride) and/or black platinum coatings. To limit the roughness to the central area only, masking techniques may be applied.

Figure 5B:
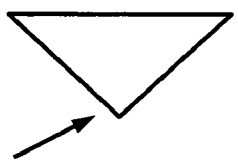

FIG. 5B is a schematic illustration of a contact with a triangular cross-section. Such a contact has an internal edge at the triangle vertex. Optionally, the vertex extends beyond the lead surface by 0.0.5, 0.1 mm or smaller or greater or intermediate amounts. A triangular contact as described in FIG. 5B can be fabricated using various methods known in the art. The other two vertexes are optionally rolled or insulated to prevent electric current density from increasing on them.

Figure 5C:
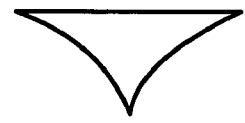

FIG. 5C is a schematic illustration of a contact with curved sides that meet at a vertex that functions as an internal edge. Optionally, the distance between the two inflection points at the two sides of the vertex is about 0.1 mm. larger sizes, such as 0.2 or 0.3 mm or smaller sizes, such as 0.07 or 0.05 mm may be used as well. Optionally, the size selected is a tradeoff between larger, for contact durability and smaller for current directionality on the plane perpendicular to the lead axis.

Figure 5D:
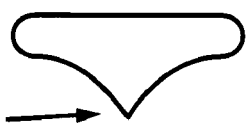

FIG. 5D is a schematic illustration of a contact's cross-section similar to that of FIG. 5C, but here the external edges are smoothed.

Figure 5E:
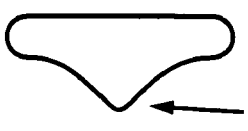

FIG. 5E is a schematic illustration of a contact's cross-section similar to that of FIG. 5D, but here the internal edge is smooth, to reduce the heat and the directionality of the field created near it in operation. A smooth vortex is a vortex having a tip having a width that is at least 10% of the width of the contact.

Figure 5F:
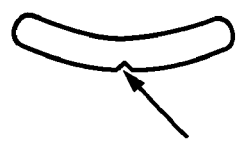

FIG. 5F is a schematic illustration of a contact with at least one groove functioning as an internal edge. Optionally, the groove is about 0.01 mm deep and 0.02 mm wide.

In an exemplary embodiment of the invention, the contact is configured to have a desired ratio (e.g., 1:2, 1:4, 1:10, 1:20) between the current exiting the smooth sections and the internal edge sections.

Figure 6A:
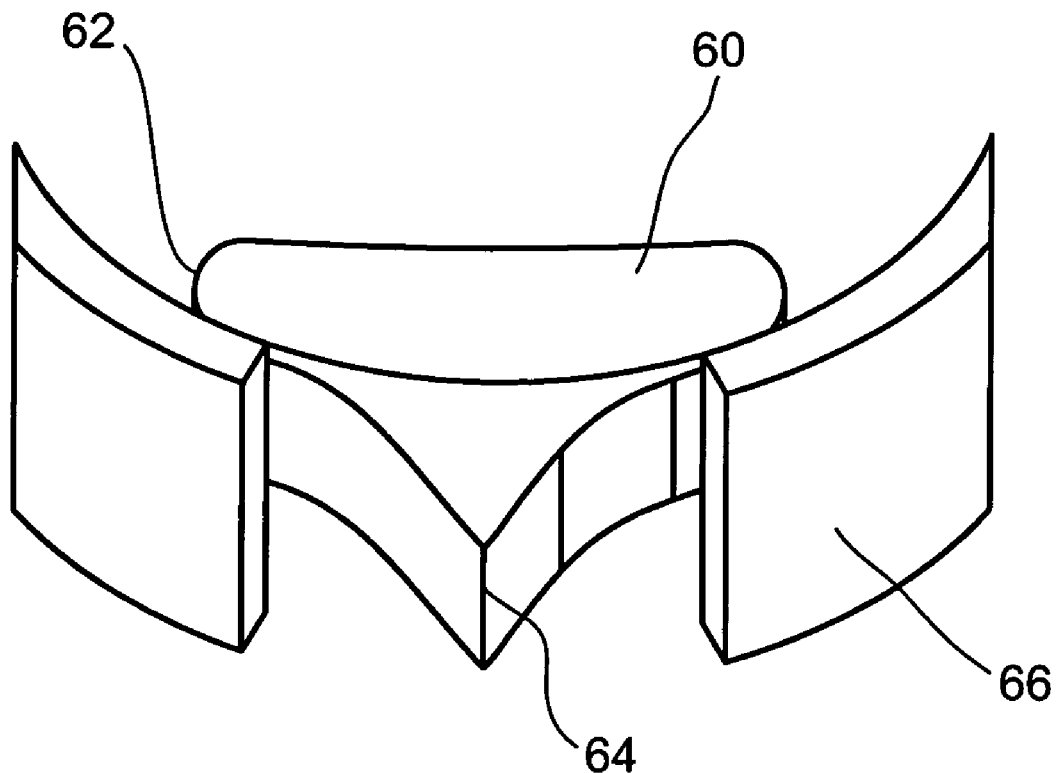
FIG. 6A is a schematic illustration of a contact having an internal edge and insulated external edges according to an exemplary embodiment of the invention.

FIG. 6A is a schematic illustration of a contact 60 with external edges 62 and internal edge 64, with the external edges being insulated with an insulating layer 66 to reduce the effect of the external edges on the tissue. The insulating layer 66 may be an integral part of the solid molded body 7 (shown in FIGS. 1 and 2) or an insulating coat applied to the external edges of contact 60.

Exemplary Preparation of Electrode Contacts

In some embodiments of the invention, the internal edges are deliberately prepared, optionally, after smoothing the outer surface of the contact. Smoothing may be helpful in ensuring that the only internal edge(s) in a contact is the one(s) prepared.

In an exemplary embodiment of the invention, a contact has a surface area of 1 mm×1 mm, and edgeless margins of about 0.2-0.3 mm along the contact periphery are left smooth. In this example, internal edges are formed only in the area within these edgeless margins. Edgeless is used herein to denote free of internal edges.

In an exemplary embodiment, contacts are manufactured from a metal tube (for example, Platinum tube) cut to segments, and optionally smoothed, for instance by electropolish, or other smoothing methods known in the art.

In an exemplary embodiment of the invention, laser percussion drilling is used to form recesses in the contact (either before or after cutting the tube for segments). The recesses are optionally of a depth smaller than the contact thickness. For example, a contact having a thickness of 100 μm is drilled to have recesses of 20%-80% of this thickness.

In some embodiments, the diameter of each recess (or mini edge) may be controlled as known in the art of laser percussion drilling, and is optionally between about 1 μm to about 20 μm, for example, 1, 5, 10, 15, or 20 μm. Smaller or larger recesses may also be useful depending, for instance, on the desirable field distribution around the contact. Generally, the more surface area the internal edge has, the more current flows through the internal edge.

In some embodiments, the shape of mini edges is controllable. For instance, mini edges having an ellipsoid, rectangular, or random form may be made.

Optionally, more than one recess is formed. For example, the entire area within the edgeless margins is covered with recesses. For example, an internal edge having the size of 520×520 μm may have 400 recesses, each 20 μm in diameter, with 25 μm spacing between centers of adjacent recesses. Optionally, the length of the recess-edges per unit area of the internal edge is between about $0.05\mu^{-1}$ to about $20\mu^{-1}$, for instance, 0.1, 0.5, 1, 5, or $10\mu^{-1}$. Internal edges of higher or smaller densities may also be useful.

Optionally, the recesses are of a constant depth and diameter. Alternatively, different recesses have different depth. Alternatively or additionally, different recesses have different diameter.

Similarly, the inter-recess spacing may be uniform, or it may vary in different places over the internal edge.

Figure 6B:
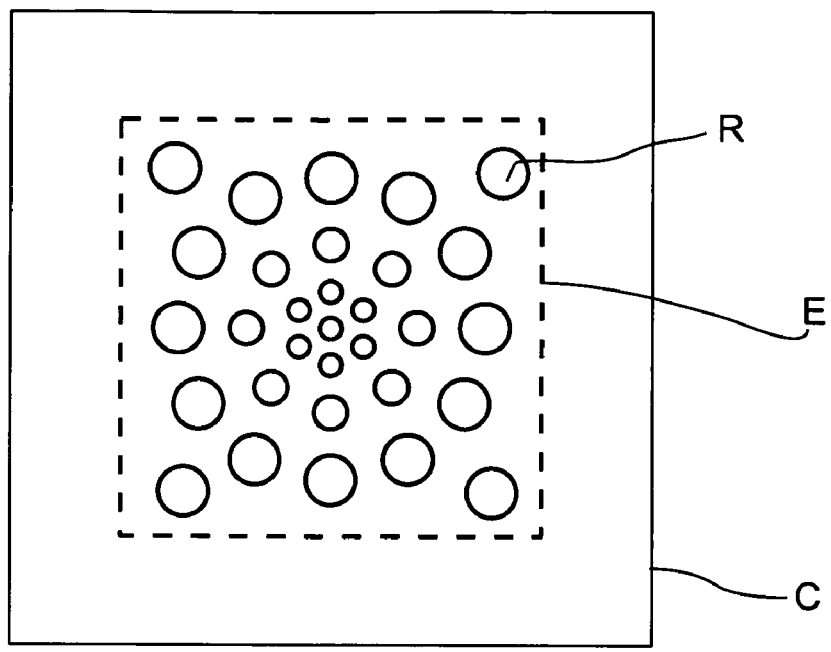
FIGS. 6B-6D are schematic illustrations of contacts according to exemplary embodiments of the invention.

FIG. 6B is a schematic illustration of a contact C having an internal edge E comprising a plurality of recesses R of different radius and density, with denser and smaller recesses at the center of the edge. Such an internal edge creates around itself field distribution similar to that created around the edges illustrated in FIGS. 5B-5F.

Figure 6C:
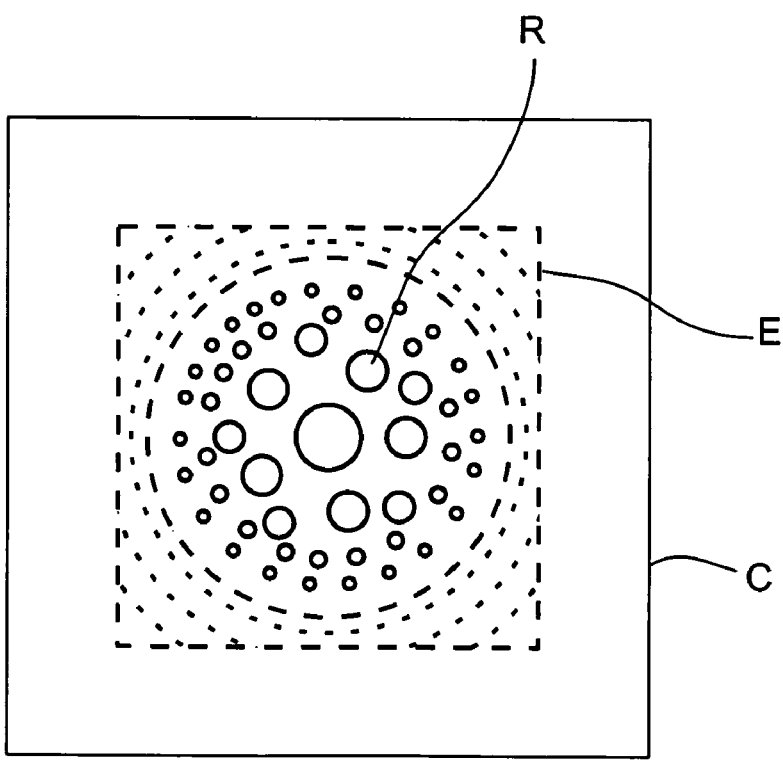

FIG. 6C is a schematic illustration of an a contact (C) having an internal edge (E) comprising recesses (R) that are larger and less dense towards the internal edge center. This internal edge creates around it electrical field of somewhat different distribution.

Optionally, recesses of uniform size but non-uniform density are formed to provide non-uniform field distribution around the electrode contact.

In another exemplary embodiment of the invention a protruding internal edge is prepared by coating a portion of a contact with a wet-etchant resisting coating, and immersing the contact in the wet etchant as to obtain a protrusion at the coated portion Thereafter, the contact is optionally dried and cleaned from the etching solution, and optionally, polished with chemical and/or mechanical polishing.

Other ways of creating internal edges comprise, but are not limited to, plasma etching, and selective coating.

Optionally, the electrical field distribution obtained around an electrode contact carrying an internal edge is measured and compared to a reference field distribution, and if some discrepancies are found, the internal edge is modified with electrical etching so as to provide a field distribution that better fits the reference one, as described below.

Exemplary Quality Control of an Electrode Contact

In some embodiments, it may be useful to ensure that the electrical field created around an internal edge is indeed the desirable one, and/or that different contacts have similar enough field distribution around them. Optionally, once the electric field distribution around a contact is defined, the contact is marked accordingly, so as to enable using it in a later stage, when a contact with the defined distribution is required. Data characterizing the field distribution around a contact may be provided, for example, as a bar code attached to the contact. This kind of quality check optionally takes place at manufacture; alternatively or additionally, it takes place in Operating Room, to ensure that the electrodes did not change (for instance, due to impact) during packaging, storage, and distribution. A system for checking the quality is described below. The system may be configured for working in manufacturing facilities or at operating rooms.

In an embodiment of the invention, when a contact is found to create a field distribution different from the one desired in more than some allowed tolerance, the internal edge shape is fine-tuned until the desirable field distribution is achieved. Optionally, mini edges are added, and/or existing mini edges are smoothed. Usually, this is more easily accomplished during manufacture than just prior to use.

In an exemplary embodiment of the invention, if a quality check prior to use shows field distribution different than expected, the obtained field distribution is optionally taken into consideration in electrification scheme design. For instance, in an embodiment of the invention, the actual electric field around each contact is used as input in the simulation discussed below in the context of FIG. 13.

Figure 6D:
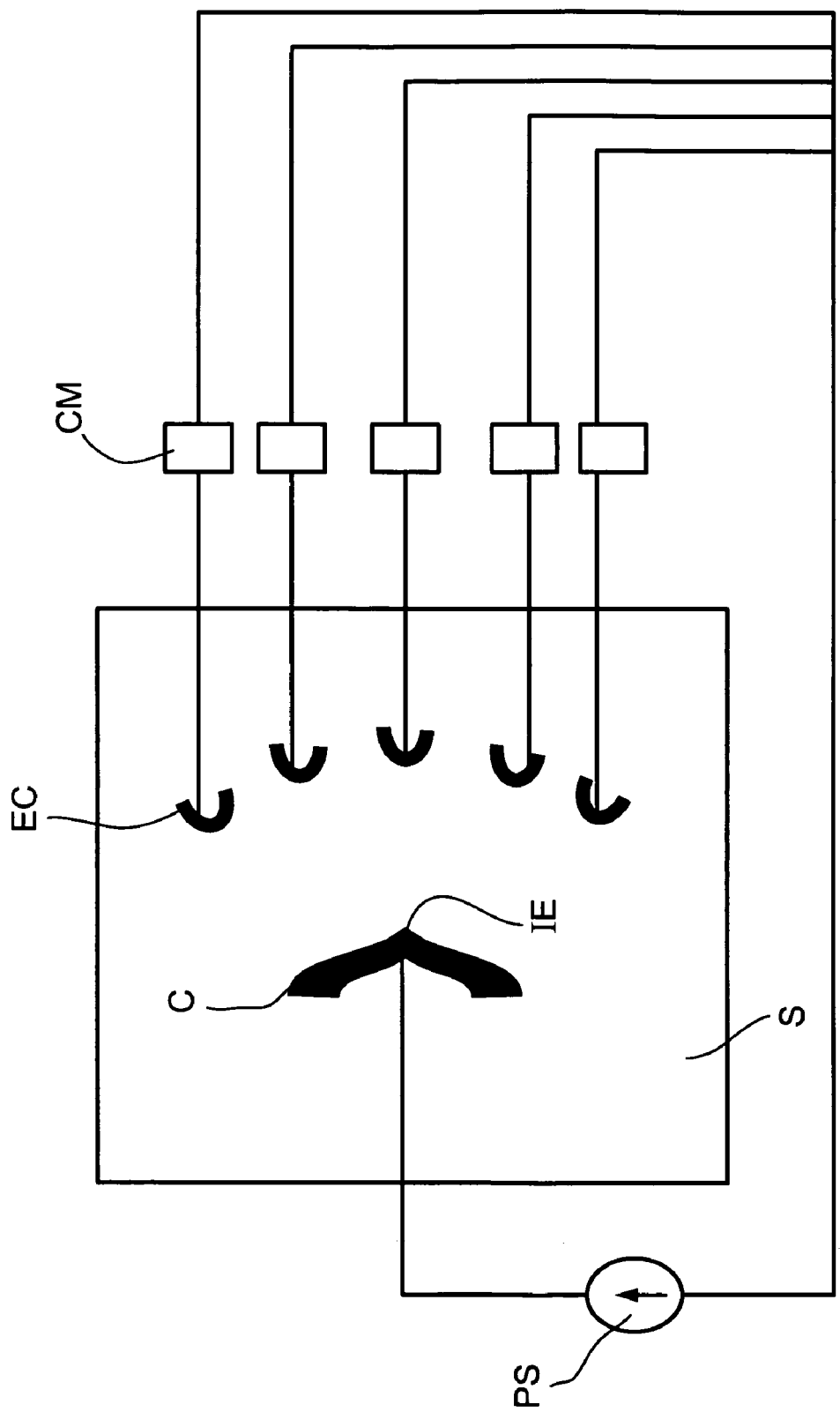

An apparatus for evaluating electric field distribution around a contact in accordance with an embodiment of the invention is schematically illustrated in FIG. 6D. Shown in the figure are a contact C, the field distribution of which is to be evaluated, and a plurality of examining contacts EC arranged around it.

Optionally, the examining electrodes are arranged around the internal edge IE at equal distances from the internal edge. In the illustrated embodiment, all the examining contacts are on a same plane. In other embodiments, they may be arranged differently, for instance, as to define a spherical shell, hemispherical shell, or the like. In other embodiments, examining contacts are positioned at various distances from the internal edge, for instance, defining several concentric hemispherical shells.

In some embodiments of the invention, the examining electrodes are moved during measurement as to measure current, voltage, or charge at different places by one electrode. Optionally, there is only one examining electrode, moved around the space to measure the distribution. Optionally, the movement is in a predetermined orbit. Optionally, the movement is along equi-potential lines.

An electric power source PS has one pole connected to the internal edge, and the other to each of the examining contacts in parallel. The power source is configured to electrify measured contact with electrification pulse of the kind expected to be applied to the same contact when the contact is used for tissue stimulation. The examining contacts are connected to the power source through meters (CM), for measuring electric current. Optionally, the field distribution is measured with meters suitable for measuring voltage, charge, or other electrical parameters, and the way they are connected to the examining electrodes would change accordingly, as generally known to a person of ordinary skill in the art.

In an exemplary embodiment of the invention, the contact C and the examining contacts EC are all immersed in a conducting medium, for example, solution, emulsion, or gel S. In an exemplary embodiment, the medium is a saline solution. Optionally, the conducting solution has a dielectric constant similar to that of the tissue, in which the electrode should operate. Optionally, the conducting solution is an etching solution, and the currents used for checking the field distribution around the contact are small enough not to cause etching of the contact during examination. On the other hand, the currents should be large enough to be detectable by the current meters used. Therefore, in some embodiments, an etching solution of appropriate activity is selected, such that no etching will take place at some detectable currents, but etching will take place at higher currents.

The different currents, voltages, or fields, read by the different meters represent the field distribution between the locations of the examining contacts.

Optionally, the value measured at each of the examining contacts is normalized to that measured at one of the contacts. In the arrangement depict in FIG. 6F, a natural choice is to normalize in relation to the current read by the central examining contact CEC.

Optionally, the quality of the examined contact is determined by comparing measured normalized currents obtained with the examined contact to those obtained with a model contact.

Optionally, if the measured field distribution is not satisfactory, the internal edge may be modified, for instance, by electrical etching, and measurement optionally repeated. Optionally, the same power source used for measuring is used also for electrical etching, but in different power parameters. Optionally, electrical etching is carried out with the examining contacts in place. Optionally, field distribution is measure simultaneously with the etching.

Exemplary Electrification Schemes

In the following, some electrification schemes and cathodal spreads they create are illustrated. In some of the figures, plan views are used to illustrate electrification schemes.

Drawing Conventions of Plan Views

In the present application, each plan view shows 20 contacts. Nevertheless, the invention is not limited to this number of contacts, and leads useful according to the present invention may have three, four, 8, 15, 20, 30, 32, or any intermediate or larger number of contacts. Generally, having more contacts allows production of more accurately focused stimulation field. Similarly, the invention is not limited to any other characteristic of the plan views. In the plan views, each of the contacts is illustrated as a square. The contacts are arranged in four columns, numbered 1, 2, 3, and 4. Each column has five rows of contacts, marked A, B, C, D, and E.

The contacts illustrated as empty squares are neutral, that is, not being connected to a power source.

A contact marked with a slanted grid is an anode, and a contact marked with diagonal lines is a cathode. Contacts through which larger current flows in operation are illustrated with denser etching.

Anodal Shielding

In the following, exemplary electrification schemes that provide focused stimulation according to embodiments of the invention, are described.

In an exemplary embodiment of the invention a system with two leads is provided: the first lead is for implantation at or near the region of interest, and the second lead is optionally for implantation farther from the region of interest, for example, a separate lead, a contact at the brain surface (and/or further along the lead towards the IPG) and/or the IPG casing.

The first lead includes two groups of electrodes: the first group includes stimulating electrodes (combination of anodes and cathodes) for providing multi-polar (e.g., bi-polar, tri-polar, quadro-polar, or more poles) stimulation to the region of interest, and the second group includes at least one anode for providing anodal shielding and/or making the net current flow of the first group anodal. The second lead has a cathode for collecting the anodal currents provided by the shielding electrode(s). As used herein, multi-polar stimulation is stimulation using a plurality of electrodes. In tri-polar stimulation for example, at least two anodes or two cathodes are provided. In some embodiments, multi-polar stimulation is provided by fast sequential bipolar stimulation with shared electrode.

In operation, the stimulating electrodes stimulate the region of interest, and the shielding electrode, electrically coupled to the cathode on the second lead/IPG case/distant return electrode, creates an anodal shield, protecting regions away of the lead from stimulation applied by the stimulating electrodes. It should be noted that in accordance with some embodiments of the invention, even if these areas are physically closer to cathodes; the mere fact that the areas see the distal end of the lead as a net anode will make them anodal areas.

Figure 7C:
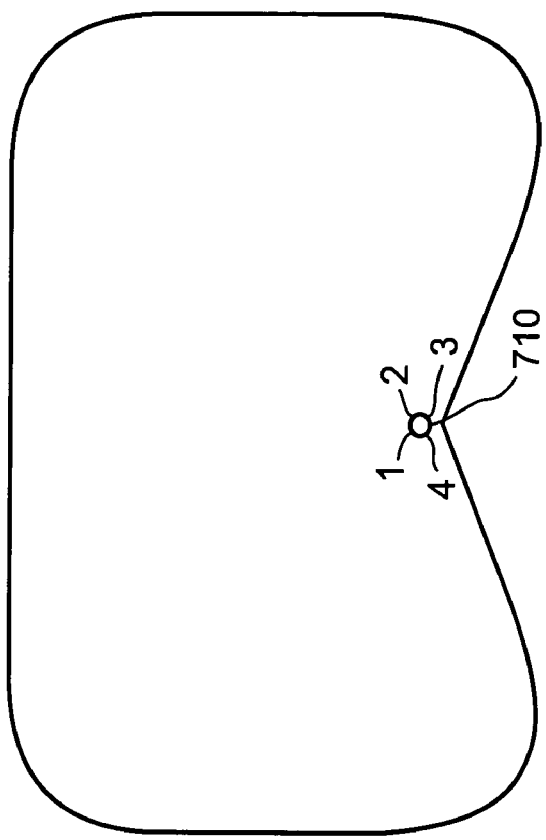
FIGS. 7C and 7D are schematic illustrations of cross sections in cathodal spreads created around the leads of FIGS. 7A and 7C, respectively.
Figure 7D:
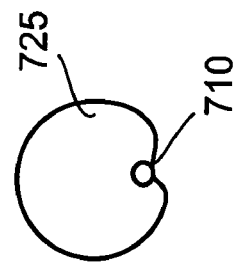
Figure 7B:
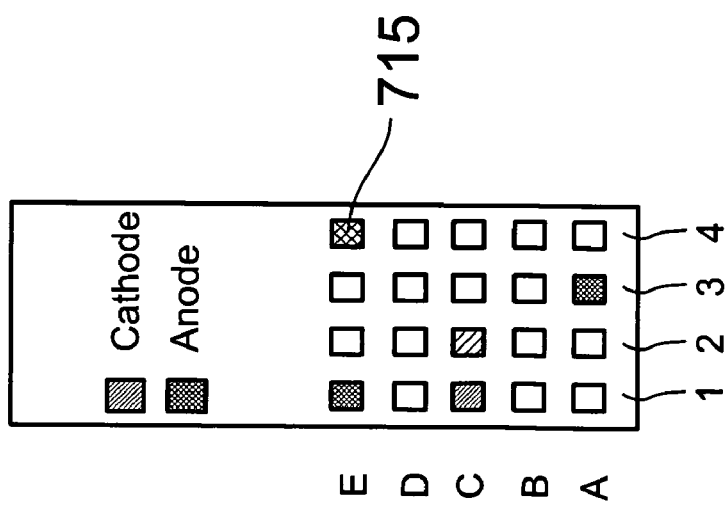
FIGS. 7A and 7B are schematic illustrations of plan views of distal portions of leads according to exemplary embodiments of the invention.
Figure 7A:
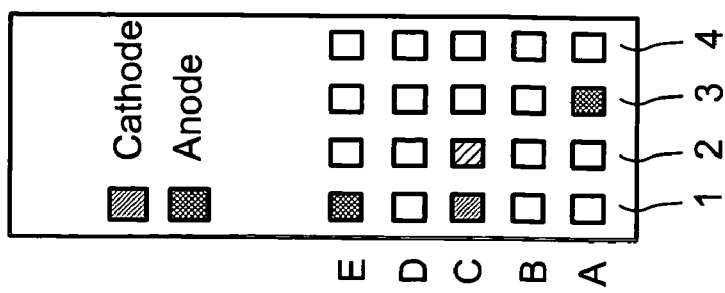

FIG. 7A is a schematic illustration of a plan view of the distal portion of a lead 710 (see FIG. 7C), which is optionally of the kind illustrated in FIG. 2.

Lead 710 has cathodes in row C, and anodes in rows A and E. Optionally, lead 710 is leaded with the center of the region of interest nearer to row C than to rows A or E. In an exemplary embodiment of the invention, the use of an anodal shield allows the stimulation area to be restricted without reducing the current used for stimulation, by the anodal shielding stopping the cathodal spread. For example, the stopping may be 5-10 mm away from the lead.

Although the anodal shielding and the spatial distribution of the stimulating contacts, as well as the current intensity flowing through each of the contacts, interact with each other in defining the final shape of the stimulation field, it is sometimes useful to design the stimulating contacts to have maximal stimulation to the region of interest, and then designing the shielding electrodes as to limit the stimulation field not to spread towards regions out of the ROI.

FIG. 7B shows a cross section 705 in the cathodal spread created around a lead 710 when electrified according to the plan view of FIG. 7A. The cathodal spreads presented here, and in other figures of invention, have been obtained by simulation, based on following assumptions: lead OD: 1.3 mm; lead distal end length: 9 mm; contact distribution along the lead: 5 rows×4 contacts in each row; total current 1-5 mA; and contact shape is simple flat segments. The cross-section is in a plane perpendicular to the longitudinal axis of the lead, at the column C. The position of the contact columns 1-4 in FIG. 7A are also presented in FIG. 7C.

Cathodal spread is the volume for which the lead provides cathodal currents that are sufficient to stimulate neural tissue.

In some embodiments, the stimulation is inhibited, at least in part, by the direct effect of anodal fields. Optionally, however, the cathodal spread itself is inhibited by anodal flow.

It should be noted, that in general, the field needed to stimulate neural tissue can vary depending on various parameters, as is known in the art, but cathodal fields are significantly more stimulating than anodal fields.

As may be noted, in lead 710 cathodes were activated only in columns 1 and 2. Accordingly, cathodal spread 705 is limited to one side of lead 710. In an exemplary embodiment of the invention, selective stimulation to an ROI is maximized by using balanced stimulation at the leads distal end (net flow from the distal end is zero) and then adding a small anodal current which is returned at a distant place to any one of the already activated anodes and/or to any other neutral contact and/or by reducing the current at any cathode, so that the distal end acts as an anode for areas distant from the lead axis. For other electrode lead designs, the "distal end" may be at a different location in the lead, for example, be one or more contacts.

Figure 7E:
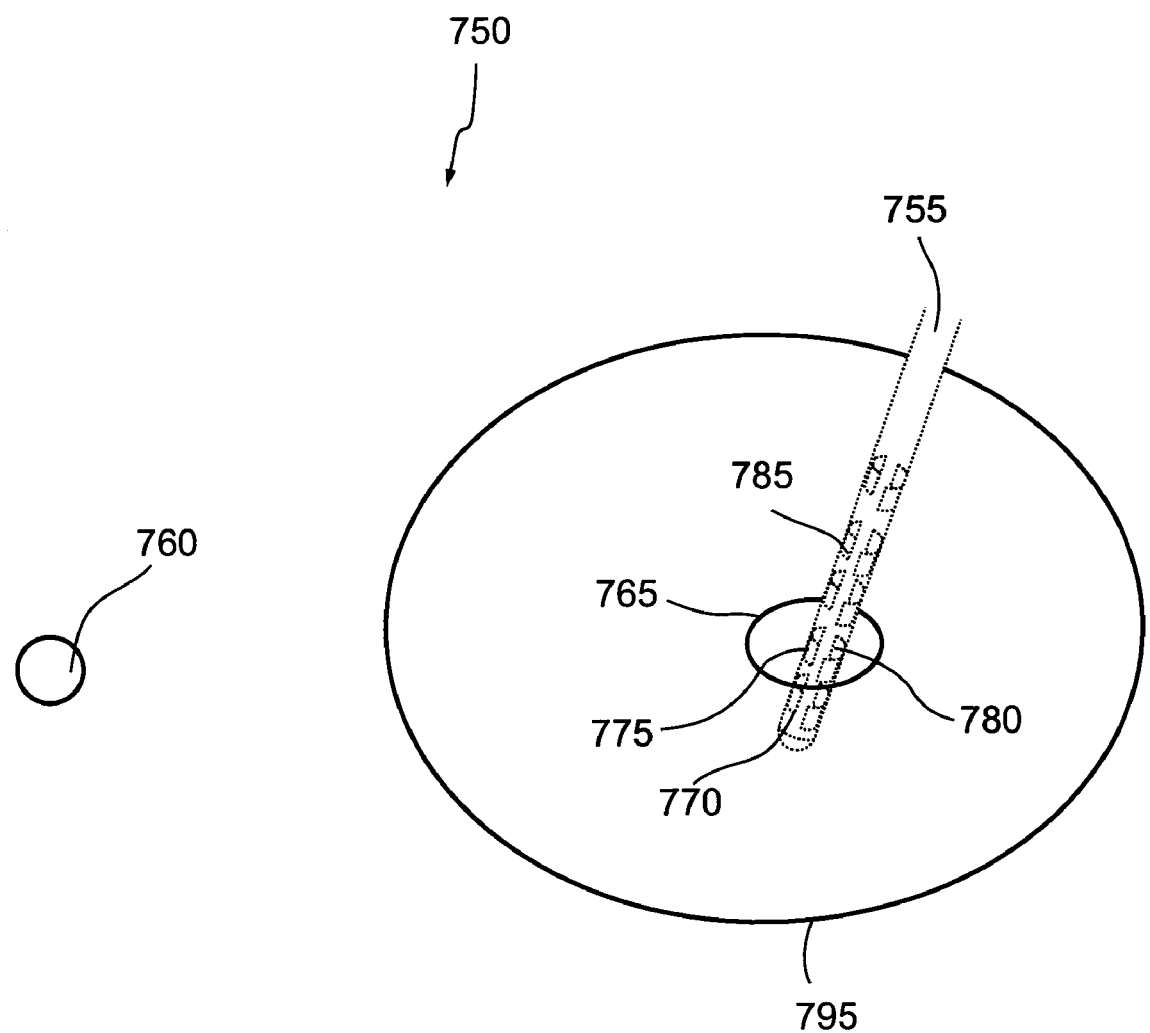
FIG. 7E is a pictorial illustration of a system for providing electrical stimulation with two leads.

FIG. 7B shows a plan view similar to that presented in FIG. 7A, but with one contact (715) dedicated to provide anodal shielding. Alternative or additionally, an intermediate contact (for instance, contact 210 in FIG. 2) may be dedicated to provide anodal shielding, depending on the size of the ROI, for example. The anodal current through contact 715 is optionally much smaller than through the other anodes. For instance, the cross-section in FIG. 7D was computed for an electrification scheme according to FIG. 7B, where contact 715 has an anodal flow of between about ⅕ to about ⅐ of the entire cathodal current flow. Currents going through contact 715 are collected by a remote. Optionally, this cathode is located on a second lead, as illustrated in FIG. 7E (760). Optionally, the casing of the IPG 25 (FIG. 1) functions as the cathode.

Optionally, from time to time, currents of opposite signs and smaller amplitudes are applied to reduce any local ionization effects and/or for discharging the accumulated charge on the electrodes tissue interface due to the application of the earlier stimulation pulse through that contact.

FIG. 7D shows a cross section 725 in the cathodal spread created around a lead 710 when electrified according to the plan view of FIG. 7B. As may be noted by comparing the cathodal spreads presented in FIGS. 7C and 7D, the anodal shielding substantially focused the cathodal spread. Without being bound to theory, it is assumed the cathodal spread focusing is achieved, because the total current flowing from the distal end of lead 710 is positive (that is, anodal), while at the vicinity of the lead there is a combination of anodal current and multi-polar stimulation. multi-polar electric fields decay with distance faster than monopolar electric fields, and thus, at large enough distances from the lead, the anodal spread is much stronger than the cathodal one, and in fact, cancels it.

FIG. 7E pictorially illustrates a system 750 for providing electrical stimulation in accordance with the anodal shield embodiment. System 750 includes two leads: 755 and 760. Lead 755 is shown inserted in a region of interest 765. Electrode contacts 770, 775, and 780 are contacts of stimulating electrodes, which for convenience will be referred to using the same numerals. Contact 785 is of an electrode (not shown, but referred with the numeral assigned to its contact, 785) dedicated to anodal shielding. At least one of electrodes 770, 775, and 780 is an anode, and at least one is a cathode. In the depicted example, electrode 770 is an anode, and electrodes 775 and 780 are cathodes coupled with anode 770. Electrode 785 is an anode (similar to electrode 770), but is coupled to a cathode comprised in lead 760. The field created between electrode 785 and lead 760 is illustrated by ellipse 795. The anodal spread created by the entire system 750 overlaps exactly with ROI 765.

In an exemplary embodiment of the invention, a single common cathode is used to provide anodal shielding to multiple sets of stimulation contacts, for example, contacts all on a same lead or on separate leads.

Tripolar Electrification Configuration

In another embodiment, hereinafter referred to as the tripolar embodiment, only one lead is optionally used, having anodes and cathodes configured to create a stimulation field of a predetermined shape and size. In the tripolar configurations, there are three groups of electrodes: a cathodes group having at least one cathode, and two anode groups each having at least one anode. Each of the anode groups is on a different side of the cathodes group along the lead axis. In a multi-polar embodiment, additional surrounding anodal groups may be provided and/or additional cathode-anode pairs may be provided between the anodal groups.

Optionally, the shape of the stimulation field obtained in accordance with exemplary embodiments of the invention is estimated by simulation. Less accurate estimation may be provided with rules of thumb. In the following passages some guidance is provided for designing electrification schemes which result in stimulation fields of predetermined shapes. In an exemplary embodiment of the invention, these methods are used as part of a process of adjusting the electrification to be as desired. A particular feature of some embodiments of the invention is that at least 1, 2, 3, or all of these adjustments can be done for a same set of electrodes being electrified. In other embodiments, electrode contacts may be added or deleted (form electrification) to achieve a desired scheme.

1. Shifting: Generally, increasing cathodal currents at contacts facing a certain direction increases the range at which stimulation will be effective along this certain direction. Similarly, increasing anodal currents at contacts facing a certain direction decreases the range at which stimulation will be effective along this certain direction. In an exemplary embodiment of the invention, to shift the center of an electrical field away of the lead without substantially changing the shape of the field, currents at contacts close to the field center are to be made more cathodic, and currents at contacts more remote from the field center are to be made more anodic.

2. Tilting: This can be achieved by increasing the anodal currents on a first group to a certain direction and increasing the anodal currents on the second anodal group in the counter direction and/or by changing the location of the anodes (e.g., put one on one side of the lead and the other on a diametrically opposite side of the lead). A virtual line may be defined between the points at the lead circumference between where the anodal current is maximal in the first anodal group to that where the anodal current is maximal for the second group. In an exemplary embodiment of the invention, the main axis of the stimulated area is perpendicular to this axis. By changing the relative currents at the two anodes, or their position and/or by using a remote electrode, this virtual line can move or be unbalanced, thereby moving the stimulation area main axis.

For example, titling can be achieved by increasing the anodal currents on members of the first group of anodes that face a certain direction and increasing the anodal currents on members of the second anodal group that face in the counter direction.

Optionally, a virtual line is defined through the lead body between a point at the lead circumference where the anodal current is maximal in the first group of anodes to a point where the anodal current is maximal in the second group of anodes. In an exemplary embodiment of the invention, the main axis of the stimulated area is perpendicular to this virtual line. By changing the relative currents at the two points, or by changing currents at other anodes, such that the position of the maximal current changes, this virtual line may be tilted, and with it the axis of the stimulation field.

3. Resizing along the lead longitudinal axis: Distancing the anode groups from the cathode group will produce a bigger stimulation field spread in a direction parallel to the lead axis. Similarly, moving the anode groups towards each other, will reduce the spread. If only one anode is moved, the spread may change only on that side.

4. Resizing along a plane perpendicular to the lead axis: using the first rule of thumb, on the cathodal group on electrode contacts in the same group will enlarge the direction of stimulation to where the cathodal currents is maximized and applying it on the anodal groups will reduce the fields on the direction where the anodal currents are maximized.

For instance, having a symmetrical tripolar arrangement of anodes and cathodes, with all the cathodal and anodal currents at the same strength provides a quasi-cylindrical cathodal spread with a spherical cross-section in a plane perpendicular to the lead. Increasing all the cathodal and anodal currents to the same extent (for example, by 20%), results in enlarging the stimulation field, without otherwise changing its shape.

FIG. 8A is a schematic illustration of a plan view of a distal end of a lead 800 according to an embodiment of the invention. As illustrated, lead 800 has anodes in rows A and E and cathodes in row C. The total current flowing from contact 800 when all the electrodes are activated as depicted in the plan view is zero, and therefore, there is no need for a collecting electrode. In other embodiments, a collecting cathode or anode (e.g., remote electrode) is used.

FIG. 8B shows a cross-section in a plain parallel to the longitudinal axis of lead 800 in a cathodal spread created by activating all the electrodes shown as anodes or as cathodes in FIG. 8A.

FIG. 8C shows a cross-section similar to that of FIG. 8B, but here, the anodes at row E are not activated, that is, all the contacts in row E are neutral. Accordingly, the cathodic spread spreads more in the direction of row E (upwards) than it does in FIG. 8B. The excess cathodal current is collected with a separate anode, not shown, optionally provided in a separate lead or a casing of a stimulator.

FIG. 8D shows a cross-section similar to that of FIG. 8C, but here the contacts of row E are activated, and those of row A are not. The cathodal spread now spreads more in the direction of row A (downwards) and less in the direction of row E (upwards).

FIG. 8E shows a cross-section similar to those of FIGS. 8C-8D, but here, only the cathodes are activated.

From comparing FIGS. 8B-8D one can note that activating anodes proximal to the cathodes diminishes the cathodal spread proximal from the cathodes and vice versa: activating anodes distal to the cathodes diminishes the cathodal spread distal to the cathodes. In this context, diminish means make smaller, but not necessarily 0. On the other hand, it was found that increasing anodal currents at contacts proximal or distal to the cathodes tilts the cathodal spread away from the proximal or distal cathodes, respectively.

FIGS. 9A-9D show cross-sections similar to those presented in FIGS. 8B-8E, but here, the separate anode is an intermediate contact residing in the intermediate portion of lead 800, rather than in a separate lead. Optionally, this can be used for further shaping of the electrical fields and return of excess anodal or cathodal currents (e.g., depending on specific electrification scheme. As may be revealed from comparing FIGS. 8B-8E to FIGS. 9A-9D, the differences between the fields obtained with the separate electrode and with the intermediate electrode are reveal some degree of tilting.

FIGS. 10A-10E illustrate the three-dimensional shape of a cathodal spread created around a distal portion of a lead, when the contacts on the distal portion are electrified as illustrated in the plan view presented in FIG. 10F.

FIG. 10A illustrates a cross-section in the anodal spread obtained in a plain parallel to the longitudinal axis of the lead.

FIGS. 10B-10E each, illustrate cross-sections in the anodal spread obtained in plans perpendicular to the longitudinal axis of the lead. Each of FIGS. 10B-10E is composed of two views: at the left hand side—a frontal view, and on the left hand side—a view from above.

The figures illustrate that the field spreads near the cathodes (FIGS. 10C and 10D) much more than near the anodes (FIGS. 10B and 10E). Furthermore, near the anodes, the field does not spread in the immediate vicinity of the lead, but only away of it (FIG. 10B). The figures also illustrates that having anodes only in one side of the lead (the most right column) results in a field that spreads mainly in one side of the lead (FIG. 10A).

FIG. 10G illustrates various properties of a cathodal spread when applied in accordance with exemplary embodiments of the invention.

An elliptical filed is shown as being generated by a circular lead with four electrode contacts on its circumference. A different number of electrodes may be provided, as noted herein. In this figure, d1 is the distance to the furthest stimulation point in the cathodal spread; D2 is the distance in the opposite direction and d3, d4 are the distances in the perpendicular direction (in same plane). Similar distances D5 and D6 can provide distance along the axis (not shown). Angle alpha shows generally the width of the spread and is defined as the angle between the points half way along D1 and the center of the lead.

The slice shown is at the level of group A (cathodes). In the following figures, also groups B and C (anodes above and below) are shown, as slices above and below group A.

In an exemplary embodiment of the invention, the field is modified by:

1. Increasing the cathodal currents on the contacts in the side of direction I, will increase d1 (j will increase d2).
2. Increasing anodal currents on groups B and C on side j will decrease d2. in some embodiments of anodal shielding and/or tri-polar stimulation, there is no stimulation at all on the j side of the lead, at least not on a plane that is wholly on the j side of the lead.
3. Increasing cathodal currents on group A in electrode contacts in the sides of directions d2, d3 will increase alpha.
4. Increasing anodal currents on groups B, C in electrode contacts in the sides of directions d2, d3 will decrease alpha.
5. In general, the group B (group C) contacts will affect alpha more if the cathodal spread is in a plane is nearer the plane of the group B (group c) contacts.
6. as noted above, d1, d2, d3, d4 can be increased or reduced proportionally by changing all the currents on all the contacts in a proportional manner.

Figure 10H:
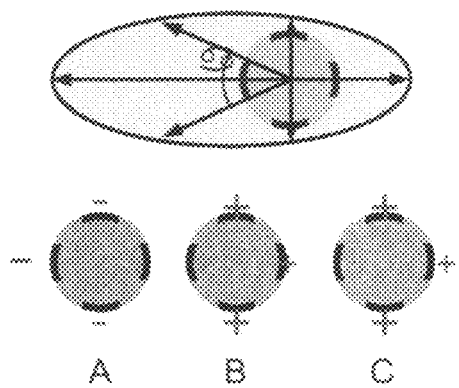
Figure 10I:
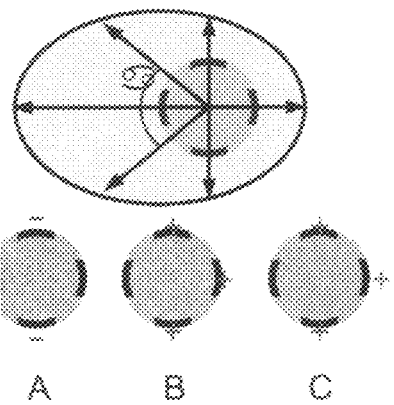

FIG. 10H, FIG. 10I and FIG. 10J illustrate various electrification schemes and their effect on the cathodal spread, in accordance with exemplary embodiments of the invention. In these schemes, A, B and C indicate planes in the lead that include the contacts of those groups and the size of the sign (+, −_ indicates the relative magnitude of current.

It should be appreciated that the same methodologies can be applied for helical leads (where the plane of electrification may be slightly oblique to the lead axis). Similarly, the electrification need not have the symmetries shown, or use the specific rows and/or row spacings shown. In general, the form of stimulation shown in these examples is semi-ellipsoid, in that it need not be an exact ellipsoid, but general has a main axis that is generally perpendicular to the lead and has the general form of a cylinder with rounded tips. Optionally, the deviation from an ellipsoid is less than +/−20% or +/−10% in distance from the center of gravity of the shape.

In an exemplary embodiment of the invention, for a lead of an OD of 1.4 mm the following cathodal stimulation field properties may be achieved (sometimes not all at once):

Length (d1) 6, 7, 8 mm or intermediate or greater numbers. D2, between 0 and 4 mm. in some cases, there is no stimulation area on the "j" side of the lead. Optionally, the imbalance between the two sides of the lead, defined as ratio of volumes on either side of a plane aligned with the lead axis is 1:20, 1:10, 1:5, 1:3, 1:2, 1:1 (no imbalance), or larger or intermediate ratios. Optionally, the ratio between the maximum width of the field and the length is 1:10, 1:5, 1:3, 1:2, 1:1 or greater or intermediate ratios. Optionally, the width at the lead (outside of the lead volume) can be 0 or 1 mm. Optionally, alpha is 30, 40, 50, 60 or 70 degrees in axial and/or transaxial extent, or smaller or larger or intermediate angles. Optionally, a tilt angle is achieved of 10, 20, 30 degrees or smaller or intermediate or larger angles.

Exemplary Electrification Sequences

Optionally, the total currents flowing from the anodes are of different intensity and/or direction than the total currents flowing from the cathodes, and an electrode positioned away of the distal end of the lead is used to collect net currents flowing out of the distal end. Optionally, a second lead (760) is provided for collecting net current flow. Additionally or alternatively, an intermediate contact (210) is used to collect net currents flowing from the distal end of the lead. Optionally, the current collecting electrode is a cathode, thus creating an anodal shield as in the anodal shield embodiment described above.

Optionally, the anodes and the cathodes are all operated simultaneously. Alternatively, the electrodes are activated sequentially. Since neural reaction to the tissue is not instantaneous, it is possible to stimulate tissue with a first electrode (or group of electrodes activated simultaneously), switch the first electrode off, and immediately switch on a second electrode. If the second electrode is switched on short enough a period after switching off the first electrode, the tissue will react as if stimulated by the two electrodes together. If there is a longer time delay between switching off the first electrode and switching on the second electrode, a different region may be simulated, possibly depending on the length of the time delay and the tissue reaction time. In some embodiments of the invention electrification sequences comprise such longer time delays. Optionally, spatial stimulation patterns are achieved using manipulation of time delay between pulses, for examples, as suggested in U.S. Pat. No. 6,988,006.

Sequential stimulation is possible with any number of electrodes activated sequentially, as long as the full sequence is short enough in relation to the reaction time of the stimulated tissue. For instance, in deep brain stimulation, a sequence is some times short enough if it is between about 60 and about 200 μsec.

It should be noted that the charge induced on the neural tissue membrane by any one of the electrodes is partially lost after the electrode is switched off. Therefore, the contribution to the field provided by each of the electrodes, depend on the position of the electrode in the sequence. For instance, electrodes that were operated first contribute less to the total field than electrodes that were activated last. Therefore, in some embodiments of the invention, the electrodes that are activated first are activated with higher voltage, to compensate for this temporal decay.

Optionally, after activating the ROI, a complimentary field is applied, having the same shape but the opposite sign, that is, where the stimulating signal was anodic, the complimentary signal is cathodic and vice versa. The complimentary field may be helpful in collecting back charge injected from the electrode into the electrode tissue interface, as to refresh the sensitivity of the tissue to another stimulation, to prevent electrode ionization, tissue injury, electrode polarization, and/or electrode destruction.

The complimentary field is optionally applied immediately after the stimulating sequence ends. Optionally, the complimentary field is applied as sequential electrode activation. Optionally, the sequence in which electrodes are activated in a complimentary sequence is reversed to the sequence at which stimulation was applied.

Handling Shortage of Current Sources

In some embodiments, each electrode is associated with a current source, and the electrodes are electrified simultaneously. However, in some embodiments, the electrification scheme requires electrifying a relatively large number of electrodes (referred to hereinafter as active electrodes), for instance, 3, 4, 5, 10, 20, or even more active electrodes, while there are only a limited number of current sources, for instance 2, 5, or 10. In some cases, the number of current sources is smaller than the number of electrodes to be electrified.

In an embodiment of the invention, the challenge of electrifying a large number of electrodes with a smaller number of current sources is met by adjusting the electrification scheme in accordance with the number of available current sources.

In a method according to an embodiment of the invention, the electrodes are electrified sequentially with a sequence of electric pulses, such that in each pulse the net current on all the electrode contacts on the lead is summed to some predetermined value. For instance, if the electrification scheme does not make use of a collecting electrode, the predetermined number is 0. If the electrification scheme is such that a collecting electrode has to collect an excess current, the predetermined number is equal to this excess current.

In some embodiments, keeping the net current in each pulse at a predetermined value requires electrifying one or more of the electrodes in portions, such that the sum of the portions is the current associated with the electrode in accordance with the electrification scheme.

In some embodiments, two or more pulses are provided, each carrying one current portions to active electrodes, and the total current portions per pulse is the same as the total current associated with all the active electrodes in accordance with the electrification scheme.

Figure 10K:
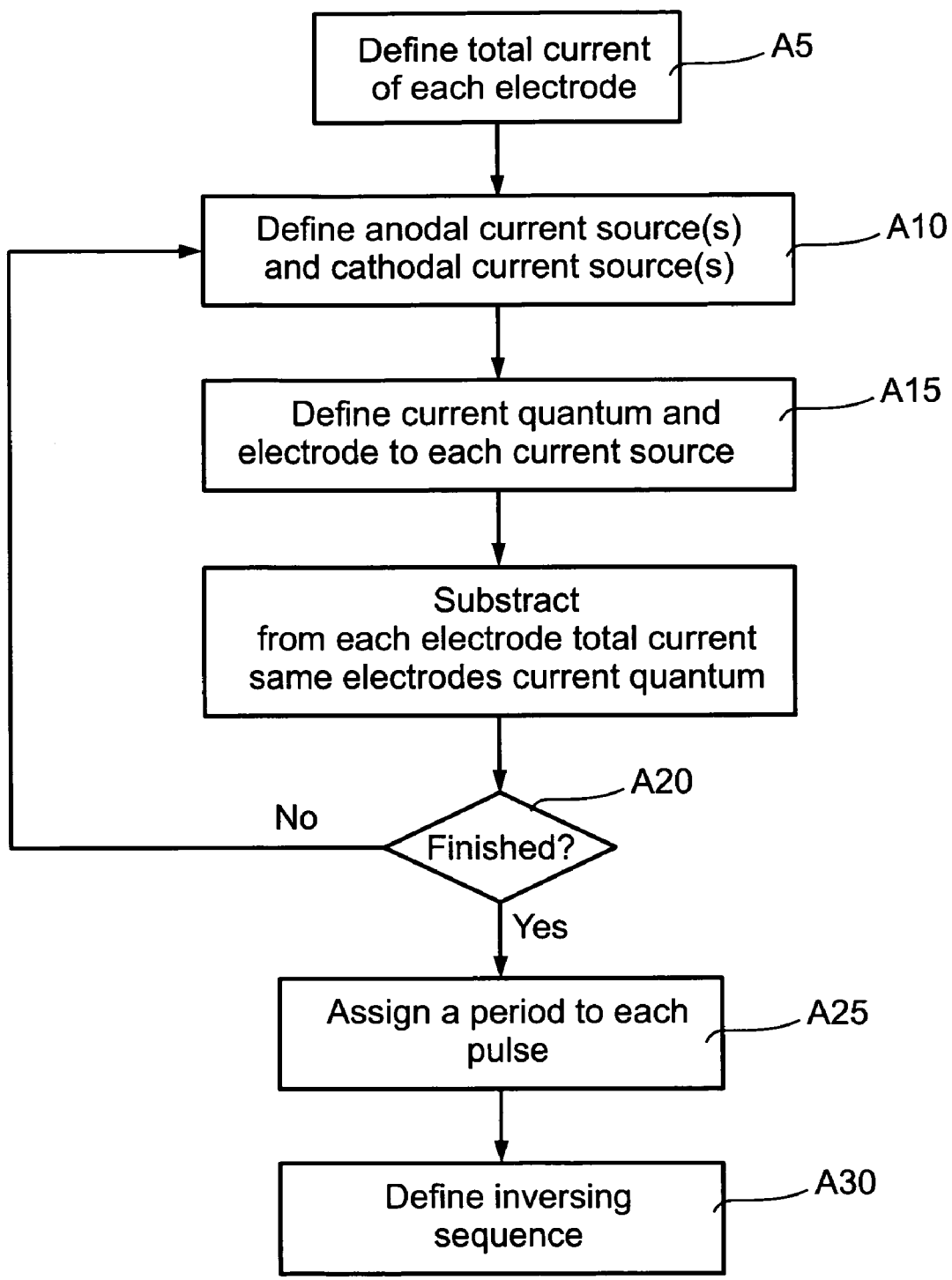
FIG. 10K is a flowchart of actions taken in a method of optimizing current source usage in accordance with an embodiment of the invention.

FIG. 10K is a flowchart of actions taken in a method of using a limited number of available current sources for electrifying a larger number of electrodes in accordance with an embodiment of the invention. In the shown method, a total current is assigned to each electrode, and provided to the electrodes in portions so as to ensure that all each electrode is provided with the total current it is assigned in a number of pulses, and the total current in each pulse is of some predetermined value. This method is optionally used in advance, in designing an electrification scheme. Optionally, the method is used in situ, when the number of available current sources is found. For instance, if a current source fails during the operation, an electrification sequence adjusted to the smaller number of available current sources may be found in situ.

At A5, an electrification scheme, associating with each active electrode a total current is defined as described herein.

At A10, current sources are defined as anodal sources and cathodal sources, responsive to the number of anodes and cathodes appearing in the electrification scheme. For instance, if the electrification scheme has more cathodes than anodes, more current sources are defined as cathodal. Optionally, the definition of a current source as cathodal or anodal changes with progress of the electrification process. For instance, a certain current source may be defined as cathodic in a first pulse, and as anodic in another pulse.

Optionally, when the number of current sources is smaller than the number of electrodes, at least one of the current sources electrifies two or more electrodes in a sequence At A15, each current source is associated with one active electrode and with a current portion the current source supplies to the associated electrode. Optionally, the assignment is such that all the current sources together are assigned some predetermined total current portion, which may be, for example, 0.

At A20, the current portion associated with each active electrode at A15 is subtracted from the total current defined to this electrode at A5. If the resulting difference is zero, the electrode is not providing any additional current portion, and the current source associated therewith is free to be associated with another electrode. If the difference associated with one or more of the electrodes is not zero, control gets back to A10, where currents and sources are assigned to electrodes as to provide the remaining of the total currents, not yet provided.

At A25, when all the differences are zero, the length of each pulse is defined. Optionally, the pulse lengths are defined such that total length is equal to some predetermined length, during which stimulations are summed by the tissue, in accordance with the electrotonus principle. In deep brain stimulation, this period is usually between 60 and 200 μsec.

Optionally, each of the pulses is assigned the same length, which is the above-mentioned total length divided by the number of pulses. Alternatively, different pulses are assigned different lengths. For example, in one embodiment, the total length is divided by the number of pulses, and then the first pulse is lengthened by some factor (for example, 10%) and the last pulse is shortened by a similar factor to compensate for possible decay of the first pulse by the time the last pulse is provided to the tissue. Additionally or alternatively, this compensation may be achieved by strengthening the current portions associated with electrodes at the beginning of the pulse.

Optionally, there is provided a table with the required compensations, in accordance with pulse length, number of pulses, and characteristics of the tissue that is to be stimulated. Optionally, this table is stored on a memory of a stimulation system according to an embodiment of the invention, an automatically used when electrification sequence is designed.

At A30, an inversing sequence (also referred to herein as a complementary sequence) is defined, optionally, equal to the stimulating sequence, but with all currents being of opposite signs, so as to collect back charge provided by the main electrification sequence to prevent, for instance, charge accumulation in the tissue.

In an embodiment of the invention, an electrification sequence is associated with each of the current sources, and this electrification sequence defines to the current source associated therewith one or more electrodes to electrify, electrification order, and current to provide to each of the active electrodes in each pulse. Optionally, the electrification sequence also defines time length of each pulse. Optionally, in each pulse, all the electrodes are electrified simultaneously. Alternatively, at least one of the electrodes is electrified after a delay, which optionally is shorter than the pulse duration.

In a preferred embodiment of the invention, the electrification sequence also defines exact timing and/or amplitude to each electrification pulse provided by a current source to an active electrode.

Optionally, the electrification sequence is designed to produce a stimulation equivalent to that achieved if all the electrodes were stimulated simultaneously.

Optionally, a collecting electrode, of the kind discussed above in the first paragraph under the heading "Exemplary electrification sequences", is considered one of the available current sources.

In some embodiments of the invention, the currents supplied by all the active electrodes (optionally, including the collecting electrode) are summed to zero. Optionally, in such embodiments, the currents are summed to zero at each of the pulses. Optionally, current assigned in the electrification scheme is provided in several different pulses, also referred to herein as current portions.

Consider, for instance, the following situation: in accordance with an electrification scheme, the cathode has to deliver 10 mA, and the three anodes are to deliver 5, 3, and 2 mA. The electrification scheme is to be applied with a system having only two current sources. One current source is devoted to the cathode, and one to the three anodes.

In a specific embodiment of the invention, in a first pulse, the cathode current source supplies a portion of 5 mA while the anode current source supplies 5 mA to the first anode; in a second pulse, the cathode current source supplies a portion of 3 mA while the anode current source supplies 3 mA to the second anode; and in the third pulse, the cathode current source supplies a portion of 2 mA while the anode current source supplies 2 mA to the third anode. Thus, the three portions supplied by the cathode sums to the 10 mA assigned to the cathode in the electrification scheme.

In a different embodiment, providing a similar electrification scheme, but with a collecting electrode providing anodic shielding of 2 mA, the cathode supplies in all the three pulses 4 mA, while the excess cathodal charge (of 1, −1, and −2 mA respectively, which sums up to 2 mA anodal shielding) is collected with the collecting electrode. As may be apparent in the last example, a current source may change its role from anodal to cathodal and/or vise versa during operation. This may be the case with the current source associated with the collecting electrode, as in the above example, or with any other current source.

In some embodiments, efficient utilization of the available current sources requires that a single electrode is sequentially electrified with two or more current sources.

Exemplary Uses

In many prior art stimulation methods, the lead must be inserted very accurately into the region of interest, since positioning the lead even 1 mm away of the place it should have been in, causes undesirable side effects. Some prior art stimulation methods are also limited in that even when the lead is perfectly placed, it is impossible to limit the stimulation to the ROI only, especially so if the user can tell the exact borders of the ROI only when the lead is in place.

FIGS. 11A-11F demonstrate advancement over those prior art methods, achievable with exemplary embodiments of the invention. These figures demonstrate that insertion of the lead to different places in the ROI allows stimulating the ROI without stimulating nearby tissue is possible irrespective of the exact location at which the lead is inserted.

FIGS. 11A-11C illustrate how a lead in accordance with an embodiment of the invention allows stimulating a motor subthalamic nucleus (motor STN, white area), without stimulating other parts of the STN (etched areas). "+" signs are shown where an anode is required, and "−" signs are shown where cathodes are required.

FIGS. 11D-11F show plan views of the electrodes on FIGS. 11A-11C, respectively, representing electrification schemes that allow the stimulations illustrated in FIGS. 11A-11C.

In FIG. 11A, the lead is shown inserted off the center and to the left of the STN. Therefore, on the lead side facing to the left, where stimulation must be restricted in order not to stimulate regions out of the STN, anodes are positioned, and the cathodes are positioned on the right hand side of the lead. The electrification scheme required for stimulating only the motor STN when the lead is positioned as illustrated in FIG. 11A is shown in FIG. 11D, showing the positioning of anodes and cathodes required for tilting the field to fit exactly into the motor STN.

In FIG. 11B, the lead is shown inserted off the center and to the right of the STN. In FIG. 11C the lead is shown inserted at the center of the STN.

Figure 12A:
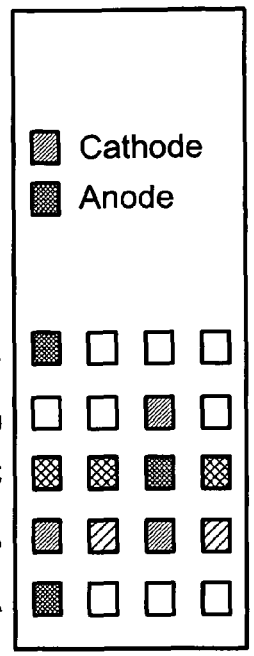
FIGS. 12A and 12B illustrate stimulating ventral intermediate thalamus in accordance with exemplary embodiments of the invention.
Figure 12B:
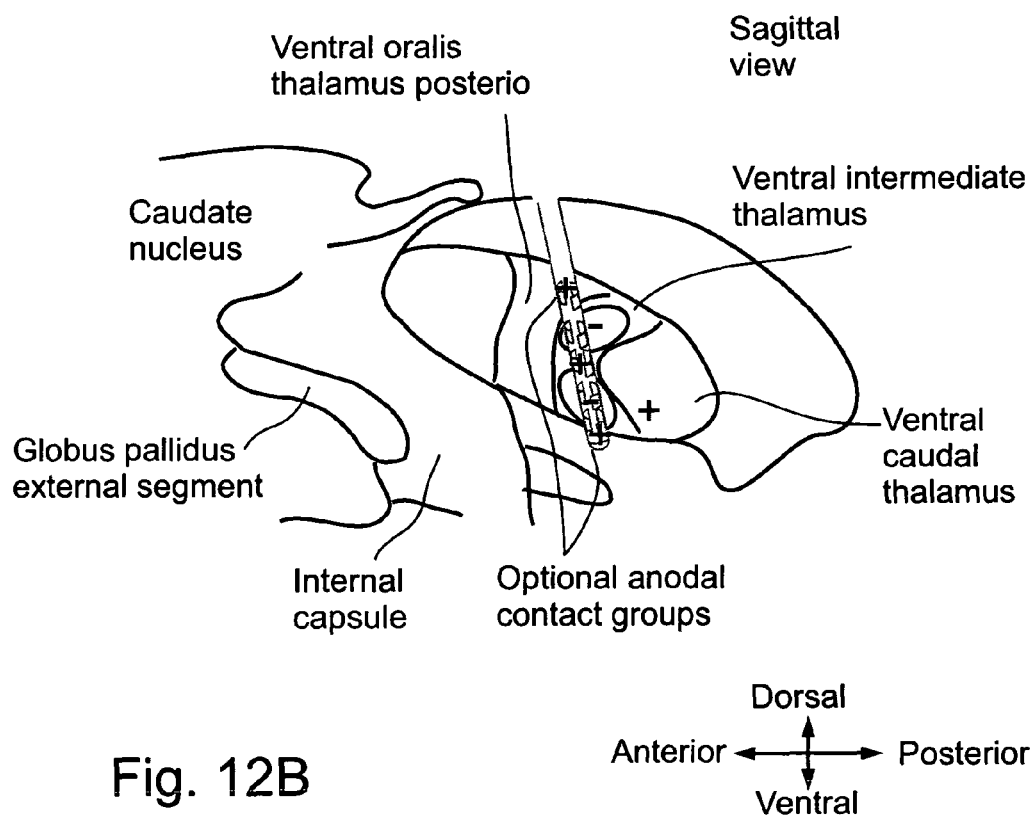

FIGS. 12A and 12B show stimulating a ventral intermediate thalamus (VIM) according to an exemplary embodiment of the invention. The VIM has a V-shape, which makes electrical stimulation of the VIM only, without stimulating neighboring tissue, practically impossible with prior art methods and devices. In accordance with an embodiment of the present invention, a stimulation field shaped as two lobes that follow the VIM V-shape is used to selectively stimulate the VIM. Conceptually, each arm of the C-shaped VIM may be treated as a separate region of interest.

FIG. 12A schematically illustrates insertion of a lead into the VIM, with "+" and "−" signs designating locations of cathodes and anodes, respectively, allowing for selective stimulation of the VIM.

FIG. 12B is a plan view of a distal portion of a lead according to a specific electrification scheme that allows for stimulating the regions of interest as shown in FIG. 12A.

It is noted that the regions of interest are in two different angles in respect of the lead. The electrification scheme includes two tripols, one for each ROI, having a common row of anodes (row C). The common row of anodes is between a row of cathodes (row B) which mainly stimulates the lower ROI and a single cathode in row D, which mainly stimulates the upper ROI. Each row of cathodes has an anode also at its other side, such that the cathodes of row B are between the anodes of rows A and C and the cathodes of row D are between the anodes of rows E and C. This way, the five rows of electrodes on the lead are electrified to create two stimulation fields, each for stimulating one ROI. And a specific electrification scheme is provided, such that each stimulation field is oriented to selectively stimulate on of the ROIs.

Exemplary Determination of Lead Orientation

As may be understood from the above examples, in many applications it may be beneficial to know the angular orientation of the lead inside the tissue, that is, which contact faces which direction. To supply a user with this information, and free him or her from having to insert the lead in a predefined orientation, the lead optionally comprises a position-orientation sensor Alternatively or additionally, the lead comprises a plurality of spaced-apart position sensors, from the output of which the orientation may be determined. This way, the position and orientation of the lead relative to the tissue dimensions can always be available to the user during insertion of the lead, and afterwards. Optionally, the position sensor operates as well known in the art based on sensing a magnetic field (which may be, for example, RF, DC, or pulsed DC) and sends in response a signal indicative of the position and orientation of the lead. Optionally, the indicative signal is sensed by a sensor, for instance, a sensor comprised in the leaded pulse generator (IPG) and/or insertion devices, and transmitted from the sensor to a processor that is configured for displaying the position and/or orientation indicated by the signal, saving it, processing it, or the like. Optionally, a baseline sensor is attached to the patient skull to allow the user determining the position and orientation relative to MRI or other images of the patient, which are optionally taken independently.

Alternatively or additionally to the position sensor, the lead itself carries a marker, the image of which by CT, MRI, X-ray, and/or any other imaging technique, is indicative of the orientation of the lead. For example, there may be provided two marks of different sizes in known places on the lead.

Alternatively or additionally, marking may be achieved as described in US 2005-0171587, the disclosure of which is incorporated herein by reference.

Determining an Electrification Scheme for a Patient

To find a suitable electrification scheme for treating a patient in accordance with an exemplary embodiment of the invention, the lead is leaded approximately in the target area, and the IPG is leaded in the chest or in the head or in any other part of the body, as known in the art per se.

The neural tissue with the lead is imaged, for instance, by CT or MRI, and the obtained image is overlaid on the patient or on an anatomical image of the patient, such that the user can see, for instance, on a screen, the position of the lead relative to the target. An anatomical atlas is optionally overlaid on the patient anatomy to make it easier for the user to visualize the target. A personal atlas, specific to the patient, is optionally used to obtain even better accuracy. The user, who optionally is a neurologist or a medical technician, explores the boundaries of the target area, optionally by performing specific stimulations using specific electrode-contacts. If side effects are detected in response to stimulations that, according to the atlas, should not have evoked the detected side effects, the atlas is optionally updated.

Optionally, a simulation for determining a suitable electrification field is then carried out. In an exemplary embodiment of the invention, the electrification parameters (e.g., temporal parameters and/or spatial parameters) are selected to match a particular disease, for example, Parkinson's disease, depression and/or dementia/memory problems. Optionally electrification parameters are optimized such that the resemblance between a required stimulation field and the stimulation field obtained by the electrification scheme is maximal.

Alternatively or additionally, the direction of the stimulating current in at least a portion of the volume defined by the field boundaries, for example, a volume occupied with neural fibers. In the brain, white material comprises neural fibers, while grey material is substantially free of neural fibers. Usually, the field threshold required for stimulating a neural fiber depends on the angle between the field and the fiber. The more parallel the field and fiber are, the weaker a field is sufficient for stimulating the fiber. Thus, a single electric field may stimulate a fiber with a first orientation while not stimulating an adjacent fiber with another orientation.

Figure 13:
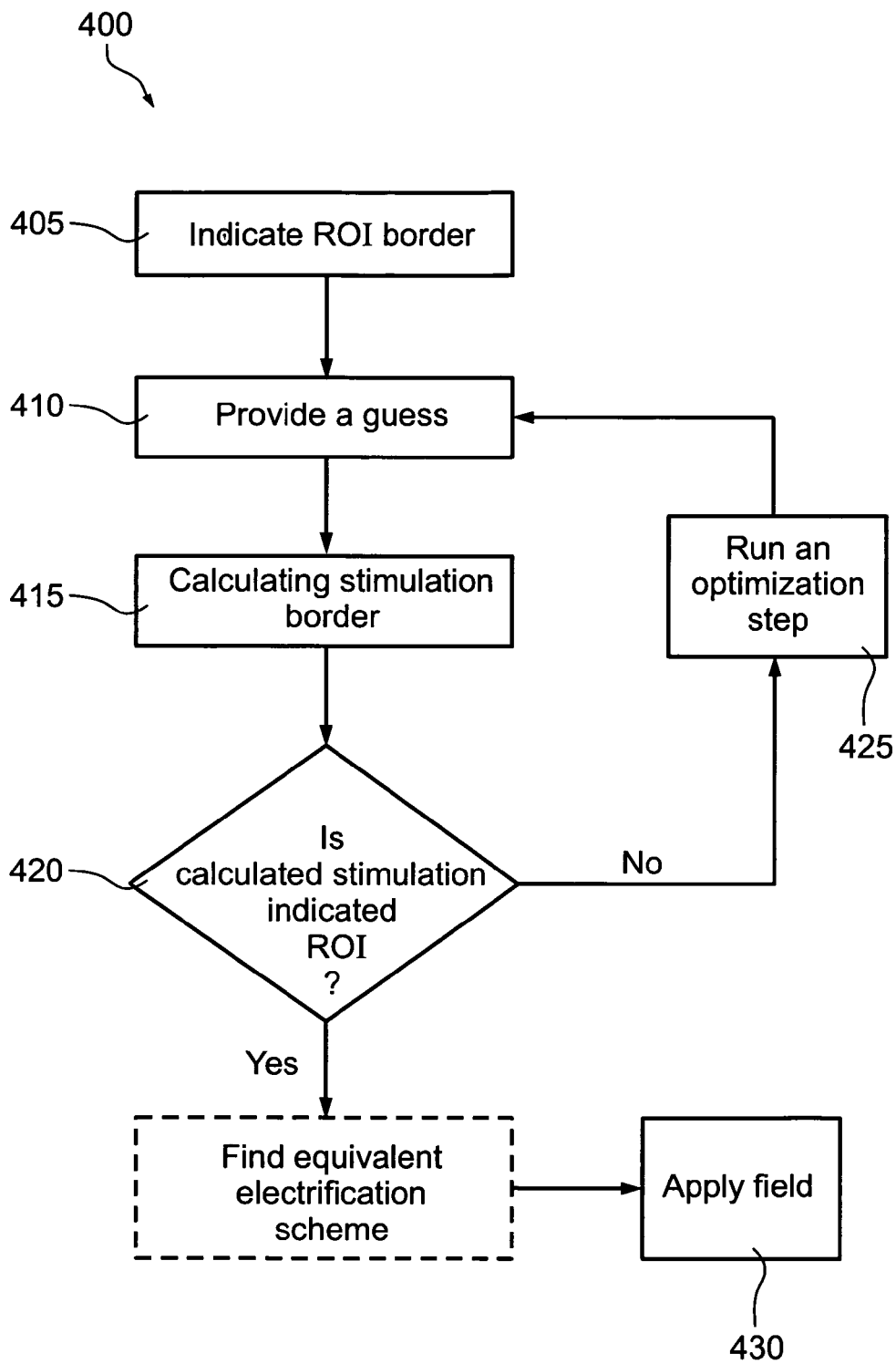
FIG. 13 is a flow chart of actions to be taken during a simulation according to an exemplary embodiment of the invention.

FIG. 13 is a flow chart of actions to be taken during a simulation (400) according to an embodiment of the invention.

At 405, the borders of the region of interest (ROI) are indicated to the system. Optionally, directions of fibers to be stimulated within the ROI are also indicated. Additionally or alternatively, directions of fibers to be non-stimulated within the ROI and/or elsewhere are also indicated. The invention is not limited to any particular method of indicating ROI borders and/or fiber directions. Optionally, the ROI borders and/or fiber directions are indicated by the user using a graphical display. Optionally, the graphical display displays an image of the patient brain with the lead leaded therein. Non-limiting examples for suitable images are CT image and MRI image. Optionally, the user activates a cursor at some points around the ROI borders.

Optionally, the activation potentials of different tissue regions at different field directions are indicated. Optionally, fibers to be stimulated and/or fibers to be non-stimulated inside and/or outside the ROI are indicated. At 410 an initial guess of an electrification scheme is suggested to the system. The initial guess is optionally suggested by the user. Optionally, the user uses former experience and/or thumb rules as described above to provide an initial guess. Optionally, the initial guess includes for each electrode contact a sign (anode, cathode, or neutral) and intensity. Optionally, the initial guess includes, for each electrode contact, electrification timing. Optionally, the intensity is expressed in potential (volts). Optionally, the intensity is expressed in current (amperes).

At 415, the processor calculates the field obtained with the guessed electrification scheme. Optionally, this calculation takes into account an electrotonus effect, whereby sequential activation has an effect similar to or different from simultaneous activation in neuronal tissue, depending on electrification timing. Optionally, the earlier activated electrodes in an electrification sequence may need higher intensity in order for the sequence to have an effect similar to simultaneous electrification, such that the higher intensity compensates for the discharge that will happen to the earlier stimulated tissue by the time other electrodes are activated. Alternatively or additionally, simultaneous stimulation is calculated.

Optionally, the processor calculates the direction of the field obtained with the guessed electrification scheme. Optionally, the processor calculates which regions are stimulated by the field and which are not. Optionally, the processor calculates which neural fibers are stimulated by the field and which are not. Optionally, calculation of stimulated and not-stimulated regions and/or fibers is responsive to differences between field direction and neural fibers direction.

Optionally, the processor calculates the field that is created by the various contacts when electrified according to the initial guess considering information on the internal edge of each of the internally edged contacts. For example, it is possible that in quality control of a certain contact it is determined that field distribution around this contact is unusual. According to one embodiment of the invention, the simulation takes this unusual field distribution into account.

Alternatively or additionally, field distribution obtained around each of the contacts is considered in the simulation, such that the simulation will be accurate also in regard of contacts having different field distributions that are all within an acceptable quality range.

At 420 the calculated field parameters are compared with the indicated ROI parameters. If they are different, a local optimization algorithm is run to suggest an additional guess (425).

Optionally, the field parameters include sign and/or intensity. Alternatively or additionally, field parameters include field direction.

Optionally, the field parameters include position of tissue excited by the field and position of tissue not excited by the field.

Optionally, the fields are compared as to be maximally similar, alternatively, the fields are compared as to be minimally different.

Optionally, required and achieved fields are compared using compatibility parameters characterizing differences (or similarities) between the fields.

Optionally, similarity comprises similarity in geometrical shape of the field, in spatial distribution of field intensity, and/or in field direction within the geometrical shape or a part of this shape.

In an exemplary embodiment, these compatibility parameters are related to parameters easily controlled with the above thumb rules. For instance, in an embodiment of the invention the compatibility parameters include a distance between the centers of the compared areas. This distance is controllable by changing the electrification scheme as described above under "shifting". Other examples for possible compatibility parameters include the angle between longitudinal axes of the two fields (controllable by "tilting"); required vs. obtained length of an axis of the electrical fields (controllable by "resizing"); and required vs. obtained current directions in some predetermined volume (also controllable by "tilting").

Optionally, a compatibility parameter is responsive to one of the above parameters, for instance, a compatibility parameter may be a squared distance, and not necessarily the distance itself, or a tangent of an angle, and not necessarily the angle itself. Optionally, a compatibility parameter is a combination of some of the above parameters, for instance, the sum or difference of two of the above parameters.

Optionally, the optimization procedure is programmed to optimize a compatibility function. Optionally, the compatibility function is responsive to an average over the different compatibility parameters. Optionally, the average is weighted. Optionally, weighting is in accordance with tolerances in different regions and/or directions. For instance, if severe side effects are expected if the stimulation field differs from the required one in a particular region, parameters that have greater effect on the field at this region are weighted more heavily.

It has been surprisingly found, that when a simulation is set to minimize the average of the above-mentioned compatibility parameters high resemblance between required and obtained field may be obtained.

Furthermore, it has been surprisingly found that satisfactory simulation results are obtained even if the obtained field is calculated only roughly, for instance, with modeling each electrode contact as a point charge or a small number of point charges, for instace 2-5. Comparison between such simplified calculations and more elaborate calculations using FEM (finite element modeling) showed that the elaborate calculation improves the optimization results only slightly, while requires a computation period longer by a factor of 100 or more on a computer with a same processing power and sufficient memory.

In accordance with an embodiment of the invention, the obtained field is calculated using a point charge model for each electrode contact. In some embodiments of the invention, an electrode contact is modeled as a plurality of point charges, for instance, 2, 3, 4, or 5 point charges.

It has also been found that the advantage of the simplified calculation over the more elaborate one is more pronounced when the number of electrode contacts is larger. Thus, a simplified calculation is especially recommended for electrode arrays comprising 5 or more active electrodes, for instance, 10, 16, or 20 electrode contacts.

Optionally, if no acceptable electrification scheme is found after some predetermined number of optimization steps or running time of the optimization program, the user is alerted, and requested to supply an alternative initial guess, required field, or acceptability limit (that is, the degree of resemblance between required and obtained fields, which is considered acceptable.)

It has also been found that the point-charge approximation is especially efficient when the electrodes used in practice have an internal edge.

When the calculated field borders (and, optionally, direction) overlap with the indicated ROI borders to a sufficient extent, or other convergence criterion is reached, the field is applied (430).

Optionally, before the field is applied, the system indicates to the user that the system is ready for applying the field, and waits for activation order from the user.

Optionally, before the field is applied or the user is prompted that the system is ready for application of the field, the processor runs a power consumption optimization, looking for additional electrification schemes with the same stimulation field borders but improved power consumption. Optionally, the optimization is selected so that the peak power required at any time is maintained below a threshold and/or minimized. Optionally, methods as described in U.S. provisional application No. 60/903,533, the disclosure of which is incorporated herein by reference is used to perform optimization and/or determine which electrodes to electrify. However, various methods of search and optimization, known in the art may be used as well.

As an alternative or an addition to the above-described optimization process, the various guesses are provided by the user rather than by an optimization program.

Optionally, a display of the borders of the electrification field calculated for each guess is overlaid on an image of the patient's anatomy with the ROI borders marked thereon. The user changes manually the guess, and finds an optimal electrification scheme intuitively.

To facilitate such intuitive optimization, a system according to an embodiment of the invention optionally has knobs (or software controls) for steering the electric field, for instance, up, down, right, or left.

Optionally, a system according to the invention has a control allowing the user to strengthen or weaken the electric field provided at each direction separately. For instance, strengthening the field going at the up and down directions, to make the cathodal spread more focused along an ellipse with a longitudinal axis parallel to the lead.

Optionally, controls for changing the intensity of the electrical field in user-defined directions are connected to a processor. The processor determines electrification schemes required for providing the stimulation indicated by the user-actuated controls, and controls the electrodes accordingly. Optionally, each of the functions that may be selected by the user (for instance, steer to the right) is associated with a predetermined change in the electrification scheme, and the user-actuated control directly invokes the predetermined change.

Alternatively, identifying the region of interest comprises identifying various different neural tissues around the lead by stimulating directed stimulations from different contacts and using the observed side-effect for compiling the anatomical map around the lead.

After the region of interest is identified, the required electrification scheme is decided, optionally by a physician with or without an aid of a suitable software. The user confirms the stimulation parameters not to exceed certain values, and communicates the required electrification scheme to the IPG, optionally, through wireless communication. Optionally, the user double-checks the patient response to the stimulation and releases the patient, or readjusts the stimulation parameters accordingly.

Optionally, deciding the electrification scheme comprises shortening arc shaped electrode contacts as to create ring contacts, and calibrating the stimulation based on patient feedback. After finding stimulation parameters that maximizes symptom relief, side effects are minimized by shutting off or grounding some of the cathodal contacts that are close the regions responsible for the side effects and/or by adding anodal contacts.

General

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A multi-contact electrode for neural tissue stimulation having an axis and comprising a plurality of electrodes going along said axis, each electrode ending with a contact, wherein at least one of said contacts has an internal edge wherein said internal edge is a feature on a tissue contacting surface of said contact adapted to concentrate a large current density relative to other regions on said contact surface.

2. A multi-contact electrode according to claim 1, configured for deep brain stimulation.

3. A multi contact electrode according to claim 1, comprising a plurality of internal edges arranged in a systematic order on an outer surface of the multi contact electrode.

4. A multi-contact electrode according to claim 3, wherein said systematic order comprises at least one of the following:
(a) having a pair of opposing contacts with the internal edges arranged such that a line connecting the centers of the internal edges intersects the axis of the multi-contact electrode;
(b) having three contacts, each with an internal edge, and the three internal edges having their centers on a plane that is perpendicular to said axis;
(c) having four contacts, each with an internal edge, and the centers of the four internal edges are on the same plane;
(d) having centers of internal edges arranged along a helix;
(e) having contacts, each with a linear internal edge parallel to said axis.

5. A multi-contact electrode according to claim 4, wherein the systematic order comprises a pair of opposing contacts with the internal edges arranged such that a line connecting the centers of the internal edges intersects the axis of the multi-contact electrode.

6. A multi-contact electrode according to claim 5, wherein said line is perpendicular to said axis.

7. A multi-contact electrode according to claim 4, wherein said systematic order comprises having three contacts, each with an internal edge, and the three internal edges having their centers on a plane perpendicular to said axis.

8. A multi-contact electrode according to claim 4, having four contacts, each with an internal edge; and the centers of the four internal edges are on the same plane.

9. A multi-contact electrode according to claim 4, wherein said systematic order comprises centers of internal edges arranged along a helix.

10. A multi-contact electrode according to claim 9, wherein said helix is of a uniform density.

11. A multi-contact electrode according to claim 1, wherein the current density at the internal edge on a contact is larger than the current density at the same contact away of said internal edge, in a factor of 10 or less.

12. A multi-contact electrode according to claim 1, comprising contacts shaped as a sector of a circular cylinder and having an internal edge.

13. A multi-contact electrode according to claim 1, wherein an electrode contact having an internal edge is a recessed electrode contact.

14. A multi-contact electrode according to claim 1, wherein said internal edge comprises a protrusion.

15. A multi-contact electrode according to claim 1, wherein said internal edge comprises a plurality of recesses.

16. A multi-contact electrode according to claim 15 having a recessed periphery, wherein said plurality of recesses are of larger density at the center of the internal edge than at said recessed periphery.

17. A multi-contact electrode according to claim 16, wherein said density gradually increases from said periphery to said center.

18. A multi-contact electrode according to claim 1, wherein at least one of said internal edges comprises a round recess.

19. A multi-contact electrode according to claim 1, wherein one or more of said internal edges has a vertex.

20. A multi-contact electrode according to claim 19, wherein said vertex is smooth.

21. A multi-contact electrode according to claim 1, wherein one or more of said internal edges is triangular.

22. A multi-contact electrode according to claim 1, wherein one or more of said internal edges has one or more curved side.

23. A multi-contact electrode according to claim 1, wherein one or more of said internal edges comprises a groove.

24. A multi-contact electrode according to claim 1, wherein said contacts are arranged in 5 rows.

25. A multi-contact electrode according to claim 1, wherein at least 50% of the contacts comprises an internal edge.

26. A multi-contact electrode according to claim 1, wherein at least 90% of the contacts comprises an internal edge.

27. A multi-contact electrode according to claim 1, packaged in a sterile packaging.

28. A multi-contact electrode according to claim 1, wherein said internal edge is located at a distance from at least one of the peripheral edges of the said contact.

29. A multi-contact electrode according to claim 1, wherein said internal edge is located at the center of the contact.

30. A multi-contact electrode according to claim 1, wherein the at least one contact in each electrode of the plurality of electrodes is shaped such that an effective distance between the contacts is a distance between the internal edges in the contacts.

31. A multi-contact electrode according to claim 30, wherein focused stimulation is increased by enlarging the effective distance between the contacts.

32. A multi-contact electrode according to claim 1, wherein the current density in the internal edge is less than 30 $\mu C/cm^2$.

33. A multi-contact electrode according to claim 1, wherein the current density in the internal edge is in a range from 150 to 1500 $\mu C/cm^2$.

34. A multi-contact electrode according to claim 1, wherein all contacts in the plurality of electrodes include an internal edge.

35. A multi-contact electrode according to claim 1, wherein a focused stimulation field of said multi-contact electrode includes an ellipsoidal volume.

36. A multi-contact electrode according to claim 35, wherein the ellipsoidal volume is more extended at one side of said multi-contact electrode than on another side.

37. A multi-contact electrode according to claim 35, wherein the ellipsoidal volume has a longitudinal axis perpendicular to a longitudinal axis of said multi-contact electrode.

38. A multi-contact electrode according to claim 35, wherein the ellipsoidal volume is non-perpendicular to a longitudinal axis of said multi-contact electrode.

39. A method of producing an electrode contact with an internal edge comprising:
  (a) providing an electrode contact free of internal edges; and
  (b) shaping the electrode contact to have an internal edge wherein said internal edge is a feature on a tissue contacting surface of said contact adapted to concentrate large current density relative to other regions on said contact surface.

40. A method according to claim 39, wherein shaping is according to a plan.

41. A method according to claim 39, wherein providing an electrode contact free of internal edges comprises:
  providing an electrode contact; and
  smoothing the electrode contact so as to obtain an electrode contact free of internal edges.

42. A method according to claim 39, wherein shaping includes roughening a portion of the electrode contact.

43. A method according to claim 39, wherein shaping comprises grooving the electrode contact.

44. A method according to claim 39, wherein shaping comprises drilling at least one recess in said contact.

45. A method according to claim 44, wherein said drilling comprises laser drilling.

46. A method according to claim 39, wherein shaping comprises electrical etching.

* * * * *